US011185554B2

(12) United States Patent
Bukreyev et al.

(10) Patent No.: US 11,185,554 B2
(45) Date of Patent: Nov. 30, 2021

(54) METHOD OF USE OF ERITORAN AS A TLR4 ANTAGONIST FOR TREATMENT OF EBOLA AND MARBURG DISEASE

(71) Applicants: EISAI R&D MANAGEMENT CO., LTD., Tokyo (JP); THE BOARD OF REGENTS OF THE UNIVERSITY OF TEXAS SYSTEM, Austin, TX (US)

(72) Inventors: Alexander Bukreyev, Austin, TX (US); Fabian Gusovsky, Tokyo (JP); Patrick Younan, Austin, TX (US); Michael Everson, Tokyo (JP)

(73) Assignees: EISAI R&D MANAGEMENT CO., LTD, Tokyo (JP); THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 16/323,888

(22) PCT Filed: Sep. 14, 2017

(86) PCT No.: PCT/US2017/051472
§ 371 (c)(1),
(2) Date: Feb. 7, 2019

(87) PCT Pub. No.: WO2018/053073
PCT Pub. Date: Mar. 22, 2018

(65) Prior Publication Data
US 2019/0275067 A1 Sep. 12, 2019

Related U.S. Application Data

(60) Provisional application No. 62/452,778, filed on Jan. 31, 2017, provisional application No. 62/395,694, filed on Sep. 16, 2016.

(51) Int. Cl.
| | |
|---|---|
| *A61K 31/7024* | (2006.01) |
| *A61K 9/00* | (2006.01) |
| *A61P 31/14* | (2006.01) |
| *A61K 45/06* | (2006.01) |

(52) U.S. Cl.
CPC ........ *A61K 31/7024* (2013.01); *A61K 9/0019* (2013.01); *A61P 31/14* (2018.01); *A61K 45/06* (2013.01)

(58) Field of Classification Search
CPC .. A61K 31/7024; A61K 45/06; A61K 9/0019; A61K 2300/00; A61K 31/14
USPC ......................................................... 514/53
See application file for complete search history.

(56) References Cited

U.S. PATENT DOCUMENTS 5,681,824 A * 10/1997 Christ ................... C07H 11/00
514/53
2007/0059318 A1 3/2007 Balu-Iyer et al.

FOREIGN PATENT DOCUMENTS

WO 2016/090404 A1 6/2016

OTHER PUBLICATIONS

Perez et al, PLOS Pathogens, 2014, 10(11), 1-17.*
Shirey et al, Nature, 2013, 497, 498-503.*
Baize et al, Clin. Exp. Immunol. 2002, 128, 163-128.*
S. Baize et al., Inflammatory responses in Ebola virus-infected patients, Clinical and Experimental Immunology, 128:163-168, 2002.
Q. Nhu et al., Novel signaling interactions between proteinase-activated receptor 2 and Toll-like receptors in vitro and in vivo, Mucosal Immunology, 3(1): 29-39, Jan. 2010.
Y. Imai et al., Identification of Oxidative Stress and Toll-like Receptor 4 Signaling as a Key Pathway of Acute Lung Injury, Cell, 133:235-249, Apr. 18, 2008.
M. Bray et al., Ebola Hemorrhagic Fever and Septic Shock, The Journal of Infectious Diseases, 188:1613-1617, 2003.
S. Berge et al., Pharmaceutical Salts, Journal of Pharmaceutical Sciences, 66:1-19, 1977.
Feldmann et al., Ebola haemorrhagic fever, Lancet 377:849-862 (2011).
Surbatovic et al., Cytokine Profile in Severe Gram-Positive and Gram-Negative Abdominal Sepsis, Scientific Reports 5:11355 (2015).
Falasca et al., Molecular mechanisms of Ebola virus pathogenesis: focus on cell death, Cell Death and Differentiation 22:1250-1259 (2015).
Tidswell et al., "Phase 2 Trial of Eritoran Tetrasodium (E5567), a Toll-Like Receptor 4 Antagonist, in Patients with Severe Sepsis", Crit Care Med, 2010, pp. 72-83, vol. 38, No. 1, Society of Critical Care Medicine and Lippincott Williams & Wilkins.
Barochia et al., "Risk of Death and the Efficacy of Eritoran Tetrasodium (E5564): Design Considerations for Clinical Trials of Anti-Inflammatory Agents in Sepsis", Crit Care Med, Jan. 2010, pp. 306-308, vol. 38, No. 1.
Opal et al., "Effect of Eritoran, an Antagonist of MD2-TLR4, on Mortality in Patients with Severe Sepsis", Journal of the American Medical Association, Mar. 20, 2013, pp. 1154-1162, vol. 309, No. 11, American Medical Association.
Menghini et al., "Toll-Like Receptor 4 Mediates Endothelial Cell Activation Through NF-κB but is Not Associated with Endothelial Dysfunction in Patients with Rheumatoid Arthritis", PLOS One, Jun. 2014, pp. 1-9, vol. 9, Issue 6.

(Continued)

*Primary Examiner* — Ganapathy Krishnan
(74) *Attorney, Agent, or Firm* — Buchanan Ingersoll & Rooney PC

(57) ABSTRACT

The present invention is directed to methods for treating ebola virus infections or Marburg virus infections comprising administering to a subject an effective amount of a compound of formula (I) or a pharmaceutically acceptable salt thereof.

Figure 1D:
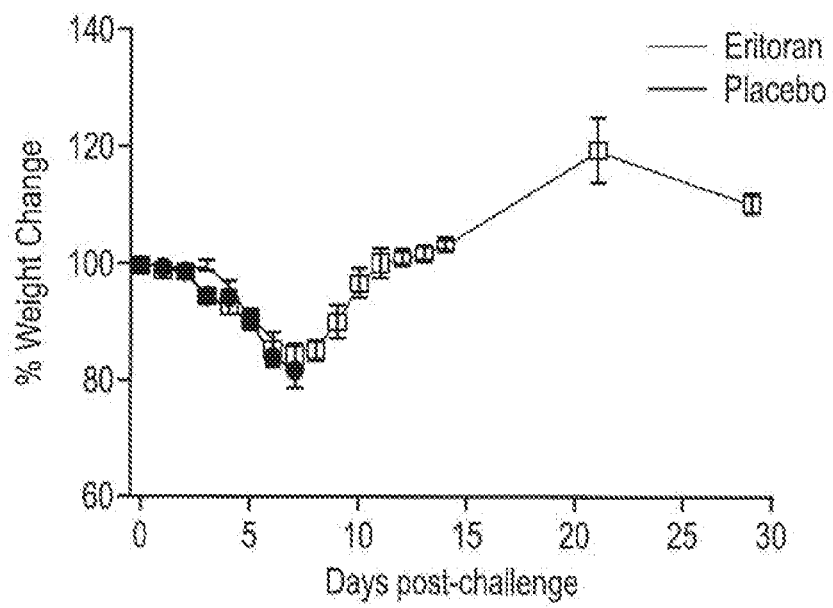

16 Claims, 14 Drawing Sheets
Specification includes a Sequence Listing.

(56) References Cited

OTHER PUBLICATIONS

Communication pursuant to Rules 161(1) and 162 EPC dated Apr. 25, 2019, by the European Patent Office in corresponding European Patent Application No. 17777120.1-1112. (3 pages).
Office Action Response dated Oct. 28, 2019, to the European Patent Office in corresponding European Application No. 17777120.1. (7 pages).
International Search Report and Written Opinion dated Nov. 10, 2017 in PCT/US2017/051472.
P. Younan, et al., The Toll-Like Receptor 4 Antagonist Eritoran Protects Mice from Lethal Filovirus Challenge, American Society for Microbiology, 8(2):1-10, Mar./Apr. 2017.
K. Shirey, et al., The TLR4 antagonist Eritoran protects mice from lethal influenza infection, Nature, 497:498-503, May 23, 2013.
J. Hellman., Addressing the Complications of Ebola and Other Viral Hemorrhagic Fever Infections: Using Insights from Bacterial and Fungal Sepsis, PLOS Pathogens, 11(10):1-9, Oct. 1, 2015.
B. Escudero-Perez, et al., Shed GP of Ebola Virus Triggers Immune Activation and Increased Vascular Permeability, PLOS Pathogens, 10(11):1-17, Nov. 2014.
C. Fox et al., A nanoliposome delivery system to synergistically trigger TLR4 and TLR7, Journal of Nanobiotechnology, 12(17):2-9, 2014.
A. Okumura et al., Interaction between Ebola Virus Glycoprotein and Host Toll-Like Receptor 4 Leads to Induction of Proinflammatory Cytokines and SOCS1, Journal of Virology, 84(1):27-33, Jan. 2010.
N. Modhiran et al., Dengue virus NS1 protein activates cells via Toll-like receptor 4 and disrupts endothelial cell monolayer integrity, www.ScienceTranslationalMedicine.org, 7(304):1-10, Sep. 9, 2015.
M. Bray et al., A Mouse Model for Evaluation of Prophylaxis and Therapy of Ebola Hemorrhagic Fever, The Journal of Infectious Diseases, 178:651-661, 1998.
S. Opal et al., Effect of Eritoran, an Antagonist of MD2-TLR4, on Mortality in Patients with Severe Sepsis, Caring for the Critically Ill Patient, pp. 1-27, Mar. 20, 2013.
J. Denner, Treatment of Ebola virus infectious with inhibitors of TLR4, Medical Hypotheses, 85:253-257, 2015.
Request of Examination dated Sep. 10, 2020, by the Japanese Patent Office in corresponding Japanese Patent Application No. 2019-507922, and an English Translation of the Office Action. (2 pages).
Voluntary Amendment dated Sep. 10, 2020, by the Japanese Patent Office in corresponding Japanese Patent Application No. 2019-507922, and an English Translation of the Office Action. (8 pages).
Petition filed on Sep. 10, 2020 with the Japanese Patent Office in corresponding Japanese Patent Application No. 2019-507922 with an English Translation. (3 pages).
Petition issued on Sep. 10, 2020, by the Japanese Patent Office in corresponding Japanese Patent Application No. 2019-507922, and an English Translation of the Office Action. (3 pages).
Office Action (Communication) dated Dec. 4, 2020, by the European Patent Office in corresponding European Patent Application No. 17777120.1. (3 pages).
Response to the Communication to Article 94(3) EPC of EP Patent Application No. 17777120.1 filed on Apr. 13, 2021.
Notice of Reasons For Rejection issued in corresponding Japanese Patent Application No. 2019-507922 dated Aug. 6, 2021, and English Translation.
Communication under Rule 71(3) EPC issued in corresponding European Patent Application No. 17777120.1 dated Oct. 8, 2021.

\* cited by examiner

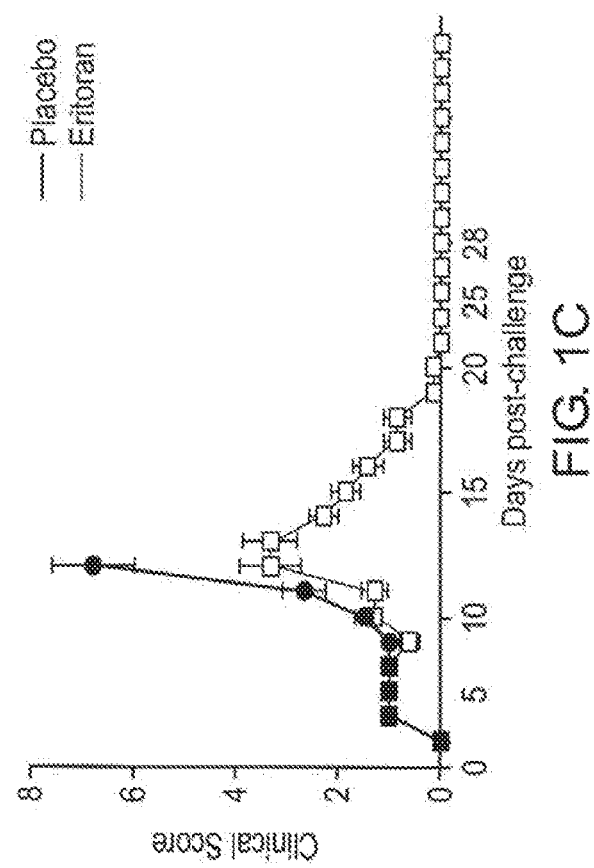
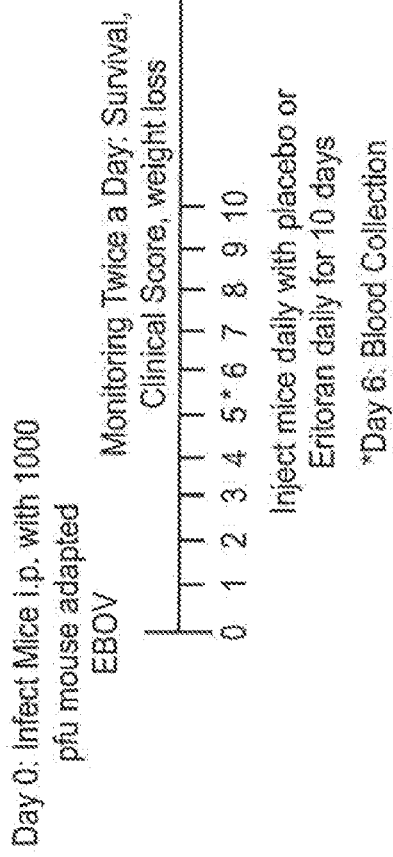
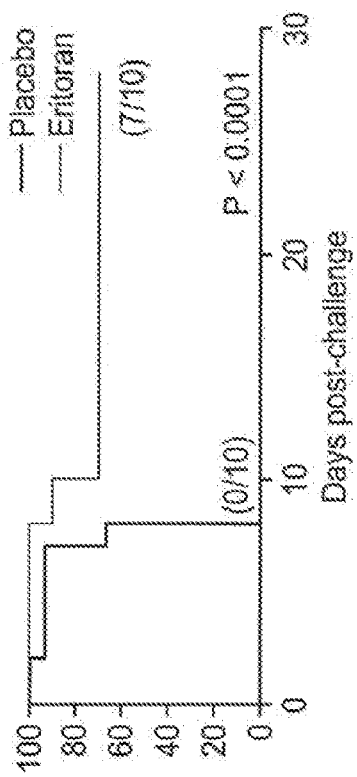

FIG. 6

| Cytokine/Chemokine | Mock | Placebo | Eritoran | P-value |
|---|---|---|---|---|
| CCL2 | 36.576 ± 8.687 | 7504.825 ± 728.643 | 6633.106 ± 1131.863 | 0.562 |
| CCL3 | 75.636 ± 11.533 | 602.400 ± 57.889 | 339.938 ± 29.833 | 0.003* |
| CCL4 | 62.655 ± 0.069 | 1849.725 ± 160.103 | 888.048 ± 134.276 | 0.002* |
| CCL5 | 39.870 ± 2.150 | 394.380 ± 37.227 | 194.702 ± 27.937 | 0.005* |
| CXCL1 | 82.384 ± 10.104 | 81.087 ± 24.075 | 806.168 ± 194.107 | 0.031* |
| CXCL2 | 161.018 ± 48.518 | 350.830 ± 42.617 | 211.766 ± 40.396 | 0.050* |
| CXCL5 | 4781.962 ± 980.175 | 663.133 ± 180.716 | 483.653 ± 37.977 | 0.386 |
| CXCL9 | 81.948 ± 15.564 | 2629.625 ± 204.219 | 1353.944 ± 71.233 | 0.0003* |
| CXCL10 | 98.646 ± 7.667 | 6827.822 ± 697.181 | 4033.86 ± 404.133 | 0.008* |
| Eotaxin | 493.456 ± 47.827 | 942.355 ± 16.581 | 944.040 ± 30.702 | 0.966 |
| G-CSF | 285.626 ± 23.515 | 1464.850 ± 239.882 | 10245.013 ± 2762.253 | 0.027* |
| GM-CSF | 28.428 ± 4.833 | 52.525 ± 6.197 | 50.328 ± 8.241 | 0.845 |
| IFNg | <1.0 ± 0.000 | 824.220 ± 81.704 | 919.904 ± 133.965 | 0.587 |
| IL1α | 125.080 ± 42.389 | 151.680 ± 31.579 | 166.850 ± 10.828 | 0.632 |
| IL1β | 23.073 ± 3.766 | 40.143 ± 5.480 | 45.347 ± 16.577 | 0.806 |
| IL2 | 14.344 ± 1.89 | 44.813 ± 10.720 | 31.978 ± 6.147 | 0.339 |
| IL3 | 1.202 ± 0.167 | 2.860 ± 1.232 | 2.158 ± 0.674 | 0.613 |
| IL4 | 0.792 ± 0.355 | 0.5 ± 0.083 | 1.048 ± 0.318 | 0.18 |
| IL5 | 21.201 ± 5.955 | 26.707 ± 6.435 | 38.560 ± 7.490 | 0.283 |
| IL6 | 4.146 ± 0.586 | 425.940 ± 126.574 | 130.334 ± 18.266 | 0.034* |
| IL7 | 11.534 ± 3.884 | 75.610 ± 12.959 | 44.930 ± 2.127 | 0.034* |
| IL9 | <1.0 ± 0.00 | 56.055 ± 1.682 | 1.294 ± 0.294 | <0.0001* |
| IL10 | 9.126 ± 1.682 | 317.492 ± 30.419 | 152.374 ± 9.454 | 0.0007* |
| IL12p40 | 48.688 ± 6.828 | 30.160 ± 13.310 | 54.460 ± 18.529 | 0.479 |
| IL12p70 | 25.484 ± 13.052 | 43.185 ± 6.636 | 54.460 ± 18.529 | 0.621 |
| IL13 | 24.570 ± 4.201 | 72.320 ± 8.175 | 48.472 ± 4.480 | 0.030* |
| IL15 | 70.546 ± 17.417 | 148.867 ± 21.582 | 147.848 ± 14.508 | 0.97 |
| IL17 | 0.572 ± 0.113 | 2.057 ± 0.482 | 2.218 ± 0.830 | 0.881 |
| LIF | 0.936 ± 0.533 | 41.873 ± 16.718 | 4.080 ± 0.428 | 0.037* |
| M-CSF | 9.214 ± 5.284 | 24.358 ± 5.642 | 38.526 ± 3.756 | 0.067 |
| TNFα | 2.472 ± 1.589 | 94.450 ± 8.443 | 50.166 ± 3.700 | 0.001* |
| VEGF | 0.832 ± 0.135 | 1.220 ± 0.125 | 1.310 ± 1.310 | 0.633 |

METHOD OF USE OF ERITORAN AS A TLR4 ANTAGONIST FOR TREATMENT OF EBOLA AND MARBURG DISEASE

STATEMENT AS TO FEDERALLY SPONSORED RESEARCH

This invention was made with government support under NIH Grants U19AI109945-01 and U19AI109664 awarded by the National Institutes of Health. The government has certain rights in the invention.

FIELD OF THE INVENTION

The present invention relates to methods for treating ebola and Marburg virus infection. In particular, the invention relates to methods that comprise administering eritoran to treat ebola or Marburg virus infection.

BACKGROUND OF THE INVENTION

Ebola virus disease (EVD), also known as Ebola Viral Hemorrhagic Fever, is a disease historically associated with sporadic outbreaks in West Africa. See *January* 2016 *World Health Organization Fact Sheet No.* 103 (http://www.who.int/mediacentre/factsheets/fs103/en/). There are five species of ebola virus (EBOV) that have been identified to date: Zaire, Bundibugyo, Sudan, Reston, and Taï Forest.

EVD includes the following initial signs and symptoms that typically start between two days and three weeks after contracting the virus: fever, fatigue, sore throat, muscular pain, and headaches. These initial symptoms are then followed by vomiting, diarrhea, rash, decreased function of the liver and kidneys, and in some cases, both internal and external bleeding. Laboratory findings include low white blood cell and platelet counts and elevated liver enzymes.

Currently, supportive care includes rehydration with oral and intravenous fluids. While treatment of specific symptoms improves survival, there is as yet no proven treatment available for EVD. Additionally, no licensed vaccines are available for EVD treatment.

As of Jun. 10, 2016, a total of 28,616 ebola cases had been reported in Guinea, Liberia and Sierra Leone, with 11, 310 associated deaths in connection with the EVD outbreak of 2014. See *Jun.* 10, 2016 *World Health Organization Ebola Situation Report* (http://apps.who.int/iris/bitstream/1 0665/208883/1/ebolasitrep10_Jun2016_eng.pdf?ua=1).

Thus, a need exists for therapeutic drugs that limit the effects of EBOV infection.

The inventors recognized that EVD exhibits several hallmarks that are associated with bacterial sepsis or what is also known as 'septic shock.' Multiple coagulopathies including Disseminated Intravascular Coagulation (DIC) due to the expression of tissue factor (TF), increased D-dimers, thrombomodulin, ferritin and thrombocytopenia are associated with both classical, bacterial induced septic shock and EBOV-induced shock (Bray et al., *J. Infect. Dis.* 188:1613-1617 (2003); Hellman et al., *Plos Pathogens* 11:e1005088 (2015)). Furthermore, immune dysfunction, lymphopenia, and systemic inflammation are also observed due to the onset of a mass, uncontrolled production of inflammatory mediators known as a 'cytokine storm' are correlative with the highly pathogenic nature of both EVD and bacterial sepsis (Bray et al., *J. Infect. Dis.* 188:1613-1617 (2003); Hellman et al., *Plos Pathogens* 11:e1005088 (2015); Falasca et al., *Cell Death and Diff* 22:1250-1259 (2015); Feldmann et al., *Lancet* 377:849-862 (2011)). Lastly, late stages of disease are associated with endothelial dysfunction and organ failure (Feldmann et al., *Lancet* 377:849-862 (2011)).

Central to the development of disease associated with bacterial sepsis, is the activation of the TLR4 signaling pathway following the detection of lipopolysaccharide (LPS) produced by gram negative bacteria. In addition, recognition of oxidized host phospholipids, which are produced following the accumulation of reactive oxygen species (ROS) upon exposure to LPS, has also been implicated as a secondary, yet potent elicitor of TLR4 signaling. Imai et al., *Cell* 1333:235-249 (2008).

Previous reports have indicated that TLR4$^-$ mice are resistant to lethal influenza challenge. Shirey et al., *Nature* 497(7450):498-502 (2013). Furthermore, Shirey et al. demonstrated that blocking TLR4 signaling protected mice from lethal influenza challenge following treatment of mice with the TLR4 antagonist, eritoran. However, implications of TLR4 signaling in the pathogenesis of EVD have thus far remained highly circumstantial.

Thus, a need exists for new therapeutic drugs that limit the effects of EBOV infection by targeting aspects of the host immune response through the TLR4 signaling pathway.

SUMMARY OF THE INVENTION

In one aspect, the invention is directed to a method for treating a patient infected with ebola virus comprising: administering to the infected patient in need of said treatment a therapeutically effective amount of eritoran or a pharmaceutically acceptable salt thereof. In one embodiment, eritoran tetrasodium salt is administered. In one embodiment, the invention further comprises administering to the infected patient a therapeutically effective amount of an antiviral compound. In another embodiment of the invention, the infected patient is administered a therapeutically effective amount of eritoran or a pharmaceutically acceptable salt thereof following testing positive for the presence of ebola virus infection. In another embodiment of the invention, the infected patient tested for the presence of ebola virus infection using PCR, rt-PCR direct antigen detection tests, virus isolation in cell culture, or combinations thereof.

In one embodiment, the invention further comprises causing a decrease in ebola-induced cytokine levels in the infected patient. In a further embodiment, the invention further comprises causing a decrease in ebola-induced cytokine levels in the infected patient wherein the cytokines comprise TNF-α, IL-6, IL-7, IL-9, IL-10, IL-13 or combinations thereof. In a further embodiment, the invention further comprises causing a decrease in ebola-induced chemokine levels in the infected patient wherein the chemokines comprise IP-10, MIG, MIP-1α, MIP-1β, MIP-2, RANTES, LIF or combinations thereof. In a further embodiment, the invention further comprises causing an increase in ebola-induced stimulating factor levels in the infected patient wherein the stimulating factor is G-CSF, KC or combinations thereof. In a further embodiment, the invention further comprises causing a decrease in granulocyte and T-lymphocyte cells in the infected patient. In yet a further embodiment, the invention further comprises causing a decrease in CD3$^+$ T-lymphocyte cells in the infected patient.

In another aspect, the invention is directed to a method for treating a patient infected with Marburg virus (MARV) comprising: administering to the infected patient in need of said treatment a therapeutically effective amount of eritoran or a pharmaceutically acceptable salt thereof. In one embodiment, eritoran tetrasodium salt is administered. In one embodiment, the invention further comprises administering to the infected patient a therapeutically effective amount of an antiviral compound. In another embodiment of the invention, the infected patient is administered a therapeutically effective amount of eritoran or a pharmaceutically acceptable salt thereof following testing positive for the presence of Marburg virus infection. In another embodiment of the invention, the infected patient tested for the presence of Marburg virus infection usingenzyme-linked immunosorbent assay (ELISA), PCR, rt-PCR, direct antigen detection tests, virus isolation in cell culture, serum neutralization, or combinations thereof.

In one embodiment, the invention further comprises causing a decrease in Marburg-induced cytokine levels in the infected patient. In a further embodiment, the invention further comprises causing a decrease in Marburg-induced cytokine levels in the infected patient wherein the cytokines comprise TNF-α, IL-6, IL-7, IL-9, IL-10, IL-13 or combinations thereof. In a further embodiment, the invention further comprises causing a decrease in Marburg-induced chemokine levels in the infected patient wherein the chemokines comprise IP-10, MIG, MIP-1α, MIP-1β, MIP-2, RANTES, LIF or combinations thereof. In a further embodiment, the invention further comprises causing an increase in Marburg-induced stimulating factor levels in the infected patient wherein the stimulating factor is G-CSF, KC or combinations thereof. In a further embodiment, the invention further comprises causing a decrease in granulocyte and T-lymphocyte cells in the infected patient. In yet a further embodiment, the invention further comprises causing a decrease in $CD3^+$ T-lymphocyte cells in the infected patient.

In one embodiment of the invention, the infected patient is administered a therapeutically effective amount of eritoran or a pharmaceutically acceptable salt thereof following the onset of clinical symptoms, wherein the clinical symptoms comprise fever, headache, sore throat, diarrhea, vomiting, muscle pains, joint pains, skin rash, internal or external bleeding or combinations thereof. In another embodiment of the invention, eritoran or a pharmaceutically acceptable salt thereof is administered by one of the routes comprising intravenous administration, intraperitoneal administration, intramuscular administration, intracoronary administration, intraarterial administration, intradermal administration, transdermal delivery, intratracheal administration, subcutaneous administration, intraarticular administration, intraventricular administration, inhalation, intracerebral, nasal, naval, oral, intraocular, pulmonary administration, impregnation of a catheter, by suppository and direct injection into a tissue, or systemically absorbed topical or mucosal administration. In a further embodiment, eritoran or a pharmaceutically acceptable salt thereof is administered intravenously. In one embodiment of the invention, the effects of administering eritoran or pharmaceutically acceptable salts thereof cause a decrease in viral titers in the infected patient.

In one embodiment of the invention, the infected patient is administered a therapeutically effective amount of eritoran or a pharmaceutically acceptable salt thereof in a range of from between about 1 µg to about 240 mg, per dose.

In another aspect, the invention is directed to a method for treating a patient infected with a filovirus comprising: administering to the infected patient in need of said treatment a composition comprising an active ingredient and a pharmaceutically acceptable carrier wherein the active ingredient comprises eritoran or a pharmaceutically acceptable salt thereof. In one embodiment, eritoran tetrasodium salt is administered. In one embodiment of the invention, the patient is infected with a filovirus family member selected from the group consisting of cueva virus, ebola virus, and Marburg virus. In another embodiment of the invention, the patient is infected with an ebola virus selected from the group comprising Bundibugyo ebolavirus, Reston ebolavirus, Sudan ebolavirus, Tai Forest ebolavirus, and Zaire ebolavirus, or combinations thereof. In one embodiment of the invention, the infected patient is administered a therapeutically effective amount of eritoran or a pharmaceutically acceptable salt thereof following testing positive for the presence of a filovirus infection. In another embodiment of the invention, the infected patient tested for the presence of filovirus infection using PCR, rt-PCR or direct antigen detection tests, virus isolation in cell culture, or combinations thereof.

In one embodiment, the invention further comprises causing a decrease in filovirus-induced cytokine levels in the infected patient. In another embodiment, the invention further comprises causing a decrease in filovirus-induced cytokine levels in the infected patient wherein the cytokines comprise TNF-α, IL-6, IL-7, IL-9, IL-10, IL-13 or combinations thereof. In another embodiment, the invention further comprises causing a decrease in filovirus-induced chemokine levels in the infected patient wherein the chemokines comprise IP-10, MIG, MIP-1α, MIP-1β, MIP-2, RANTES, LIF or combinations thereof. In another embodiment, the invention further comprises causing an increase in filovirus-induced stimulating factor levels in the infected patient wherein the stimulating factor is G-CSF, KC or combinations thereof.

BRIEF DESCRIPTION OF THE DRAWING FIGURES

Figure 1E:
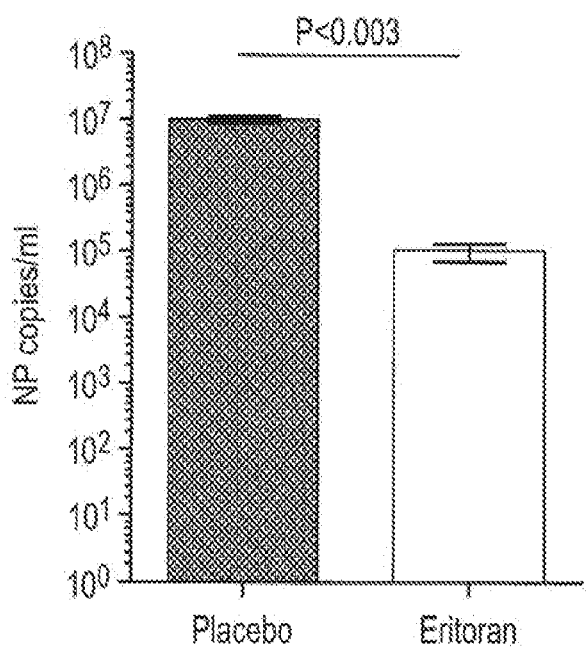

FIG. 1. Eritoran protects mice from lethal ebola virus challenge. (A) Overview of studies investigating the use of eritoran as a therapeutic for ebola virus (EBOV) infection. C57BL/6J mice were challenged via intraperitoneal injection with 1000 pfu of mouse adapted EBOV. Mice received daily injections with Placebo (vehicle) or 233 µg eritoran via intraperitoneal injection for a total of 10 days. (B) Survival curves of mice treated and monitored as indicated in (A), were generated using cumulative data from two independent experiments consisting of two groups of 5 mice. (C) Clinical scores were assigned as described in the Examples. (D) % Weight change in days following EBOV-challenge. (E) Viremia on day 6 post-infection in eritoran-treated and control mice. Mean values±SE based on 4 mice in placebo group and 5 mice in eritoran-treated group.

Figure 2A:
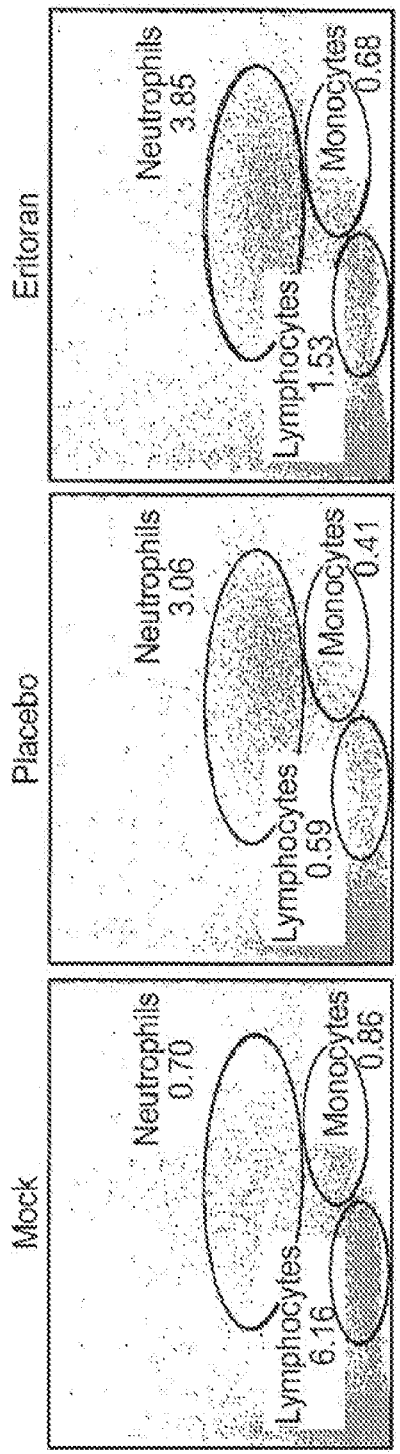
Figure 2B:
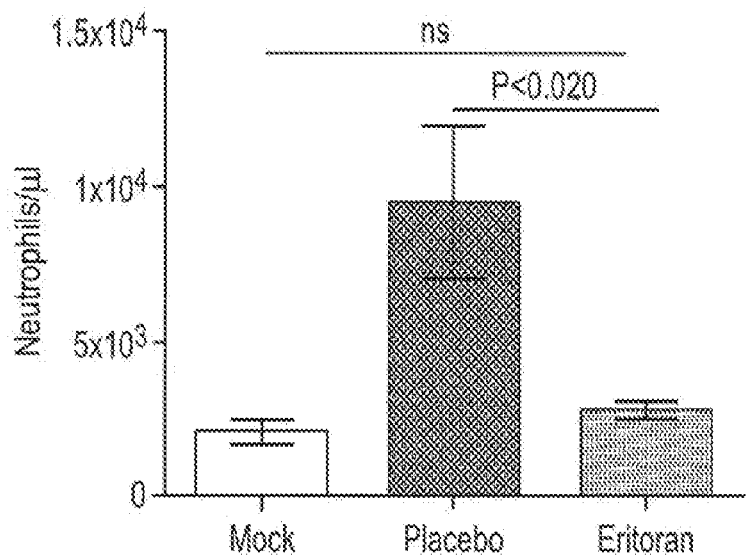
Figure 2C:
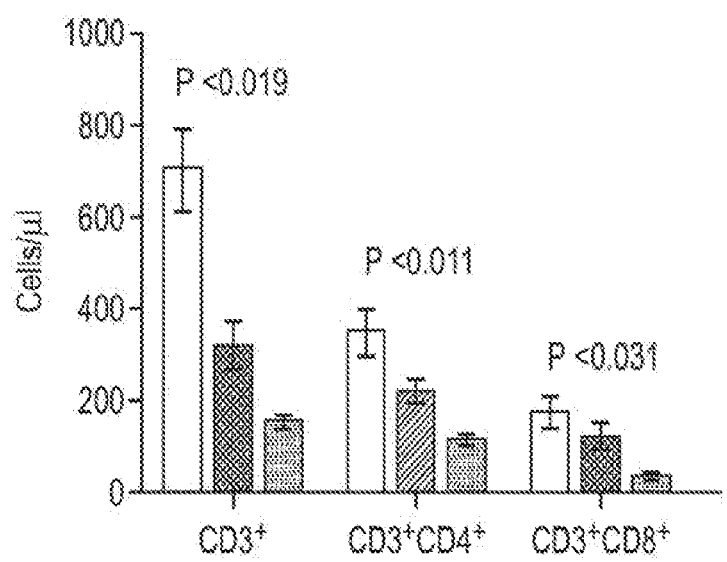

FIG. 2. Eritoran treatment reduces granulocyte and T-lymphocyte levels. (A) FSC versus SSC plots demonstrate an increase in the granularity of granulocytes (neutrophils) and absolute counts in EBOV-infected mice, which is indicative of neutrophil activation and mobilization. (B) Absolute neutrophil counts. (C) Absolute counts of $CD3^+$ T-cell subsets in white blood cells isolated from mock, placebo, and eritoran-treated mice. Regarding FIGS. 2B-2C, analysis was performed at Day 6 post-EBOV-challenge.

FIG. 3. Eritoran treatment reduces the levels of free radicals. (A) Reactive oxygen species/reactive nitrogen species (ROS/RNS). Average fold difference versus uninfected placebo-treated mice, mean values±SE based on 5 mice per group (mock, eritoran on all panels and placebo). * $p<0.05$ compared to placebo.

Figure 4A:
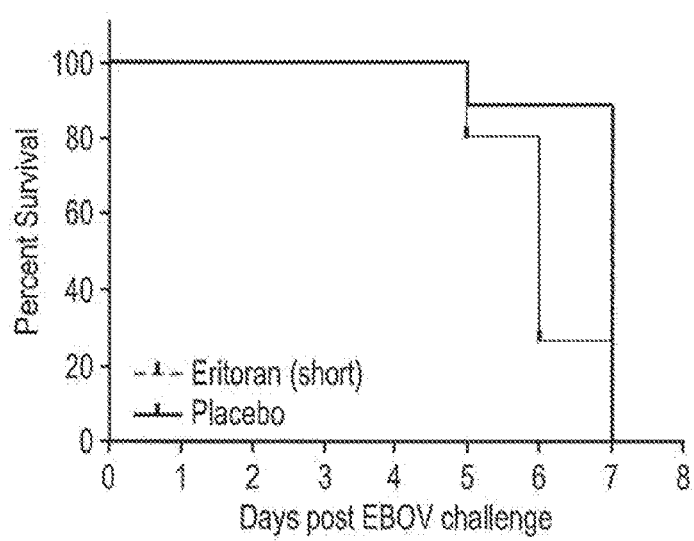
Figure 4B:
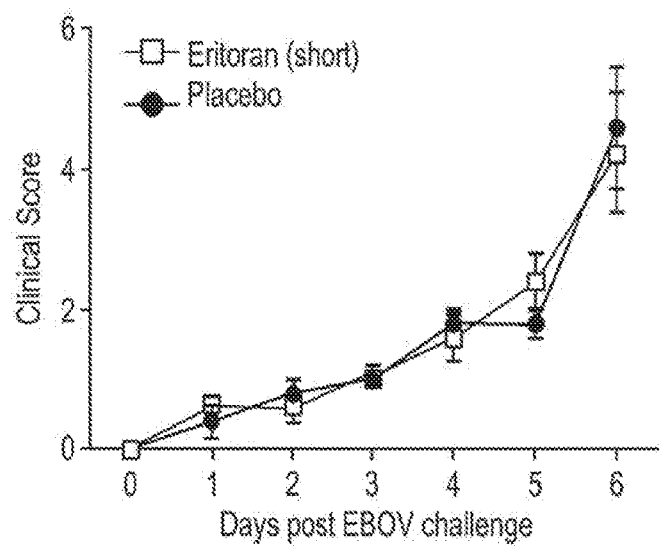
Figure 4C:
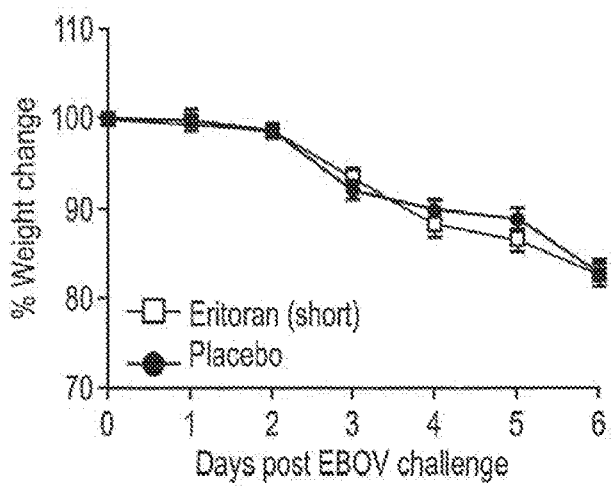

FIG. 4. Reduced duration of eritoran treatment does not protect mice against ebola virus challenge. C57BL/6J mice were treated with eritoran or placebo for 4 consecutive days starting at day 0. (A) Survival scores. (B) Clinical scores. (C) Weight. Mean values±SE based on 5 mice per group.

Figure 5:
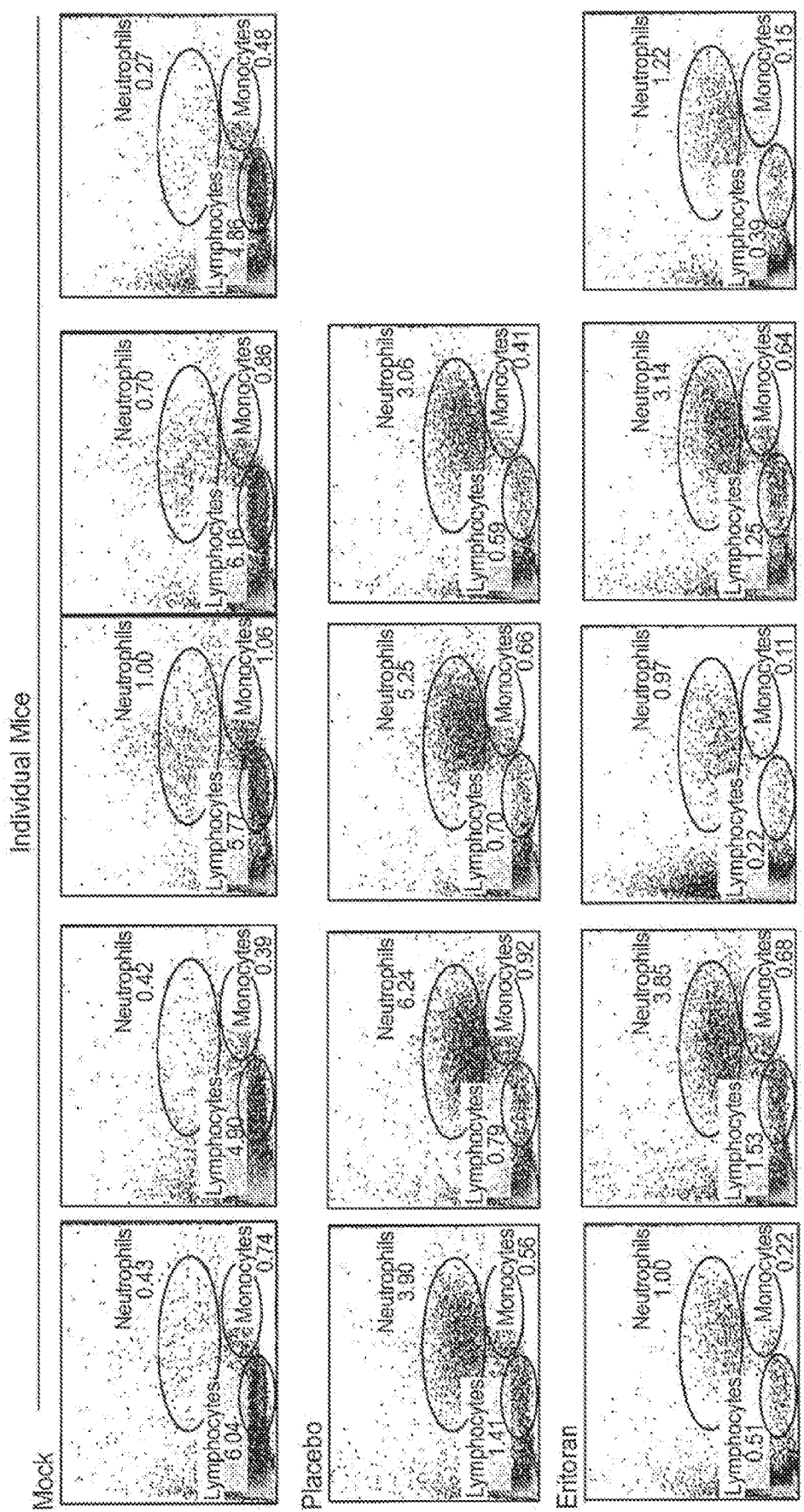
Figure 7A:
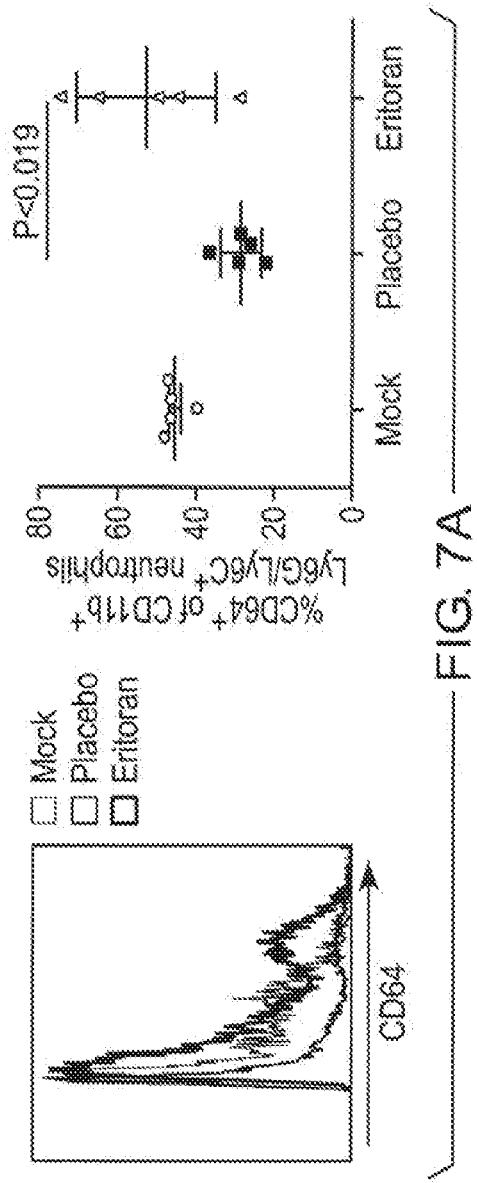
Figure 7B:
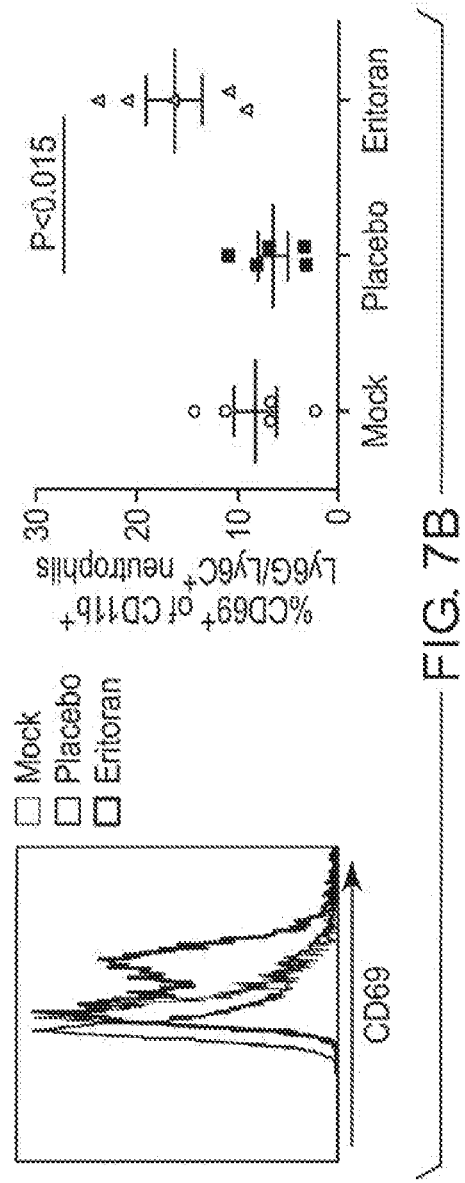
Figure 7C:
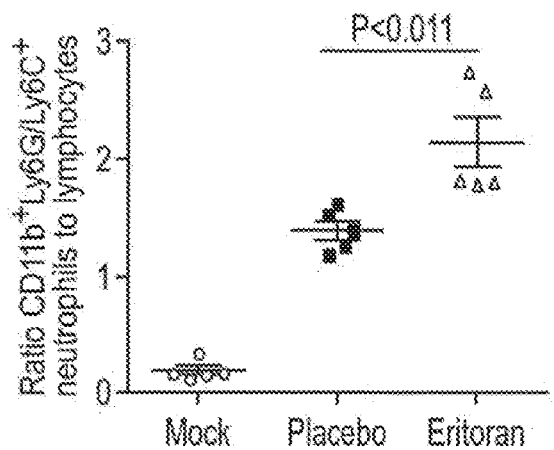
Figure 7D:
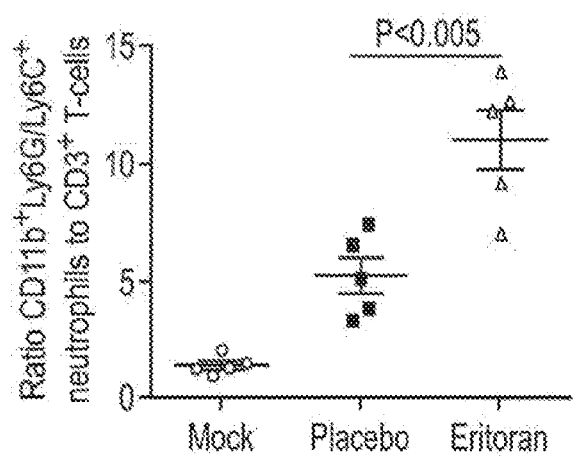
Figure 7E:
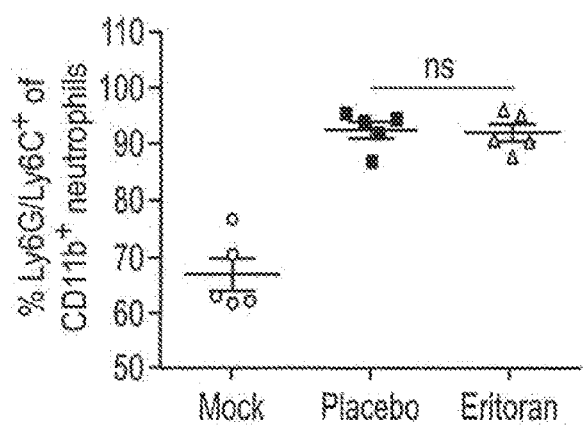
Figure 8A:
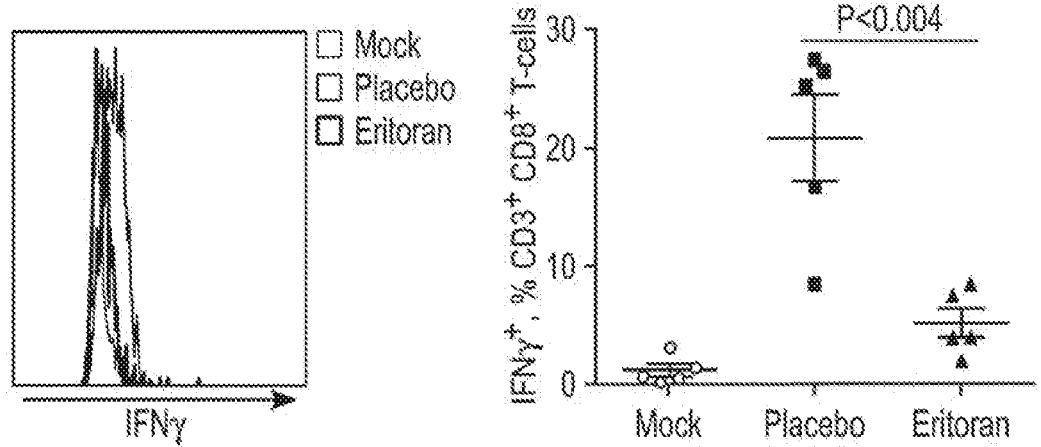
Figure 8B:
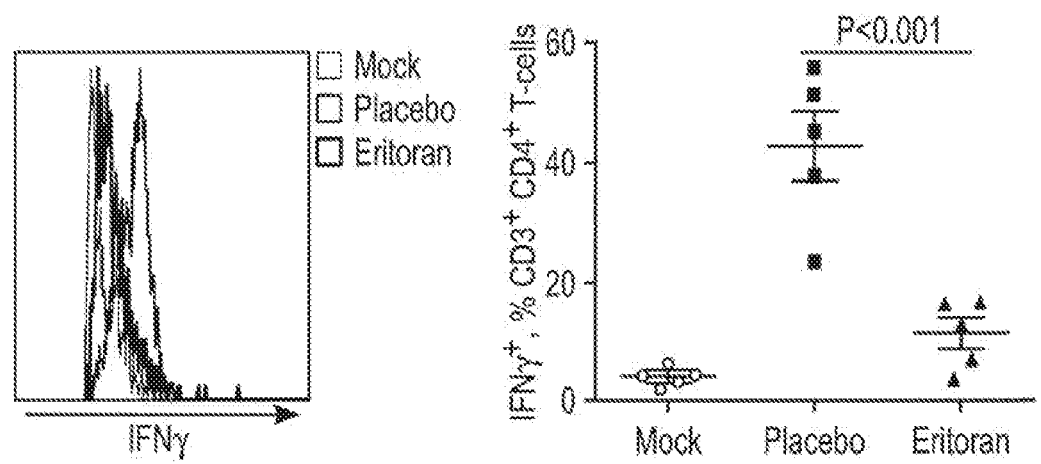
Figure 8C:
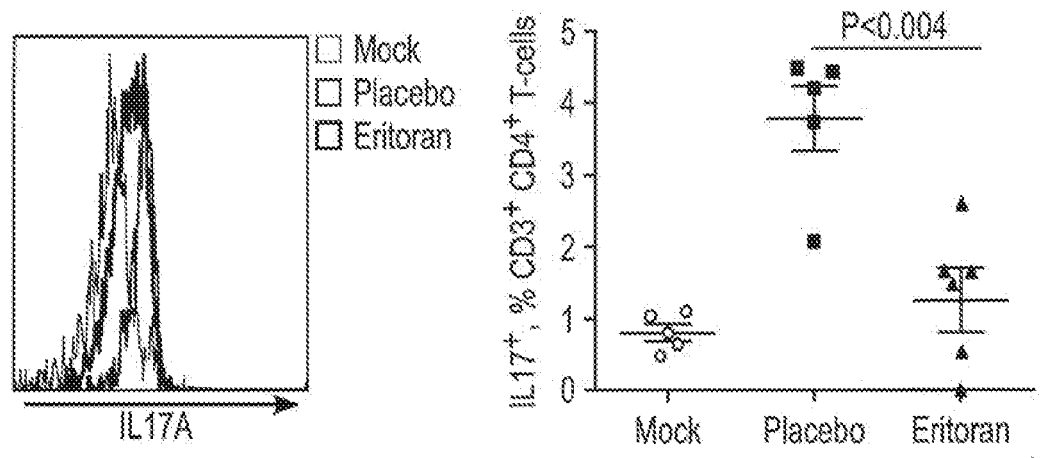
Figure 8D:
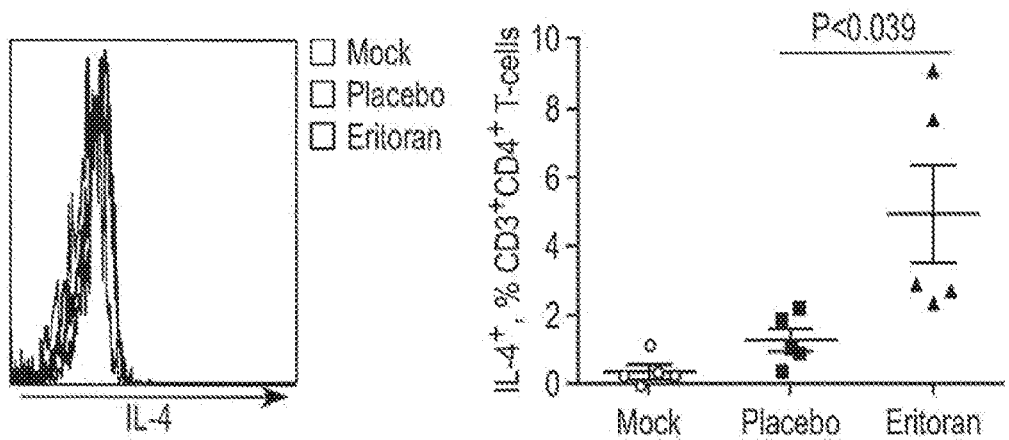
Figure 8E:
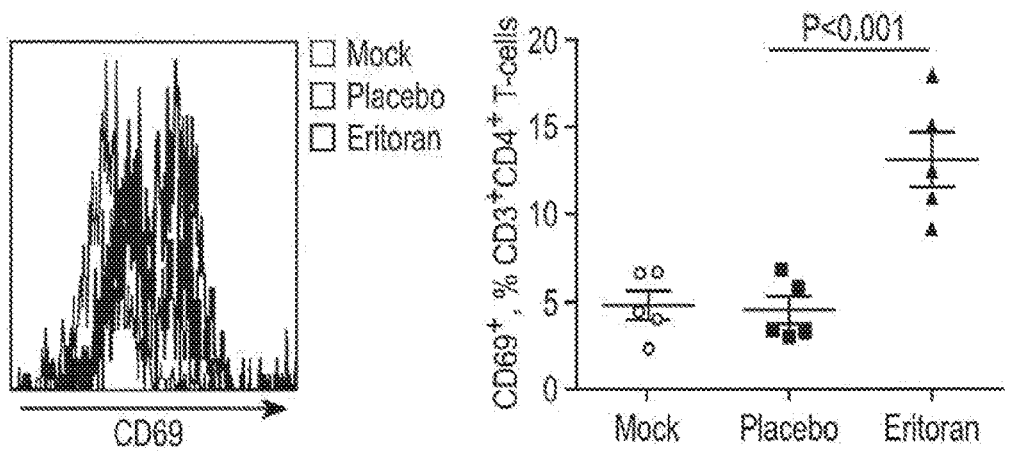
Figure 8F:
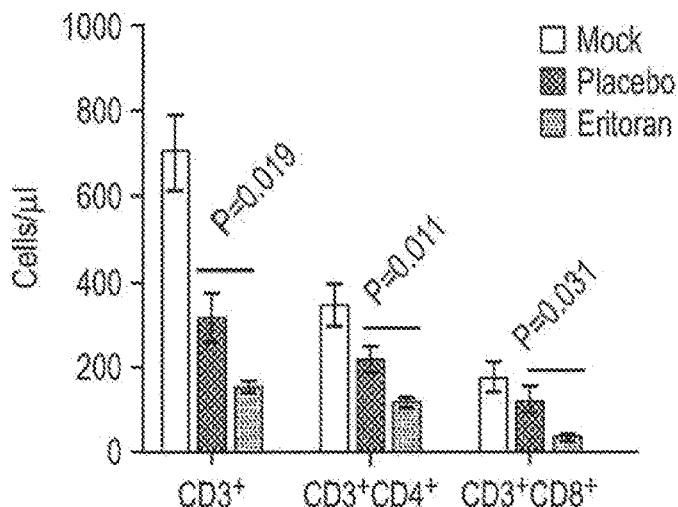
Figure 9C:
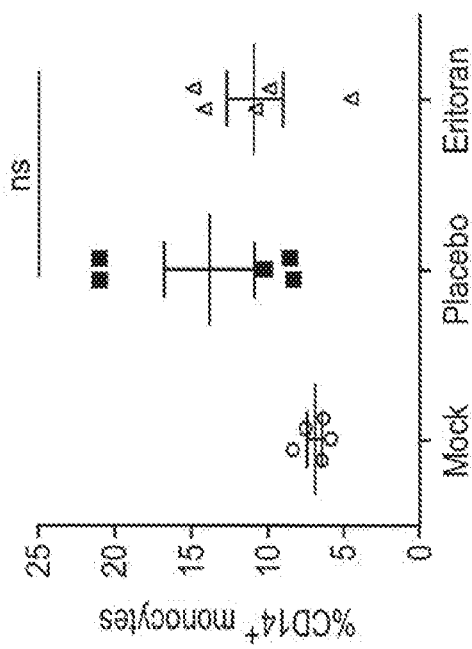
Figure 9D:
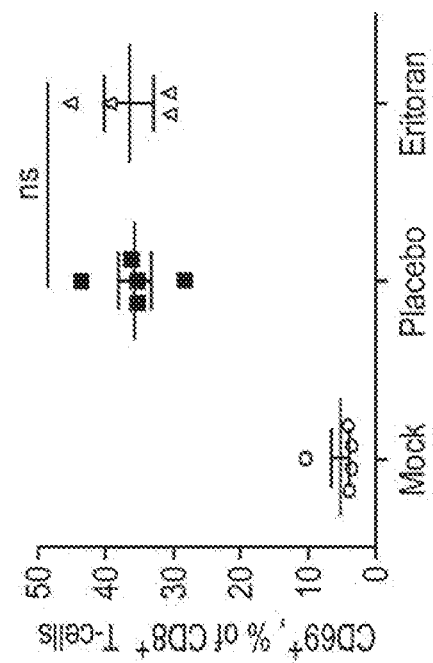
Figure 9A:
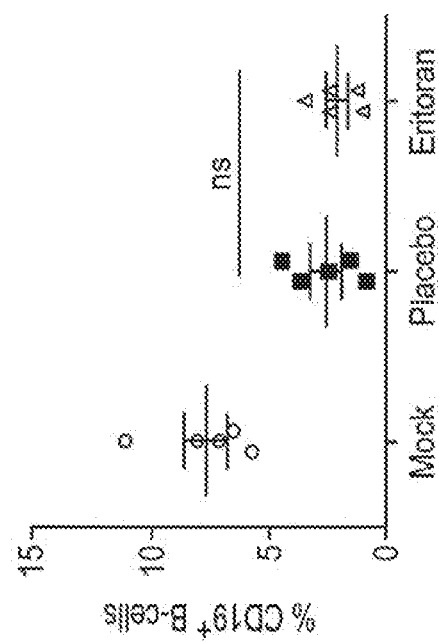
Figure 9B:
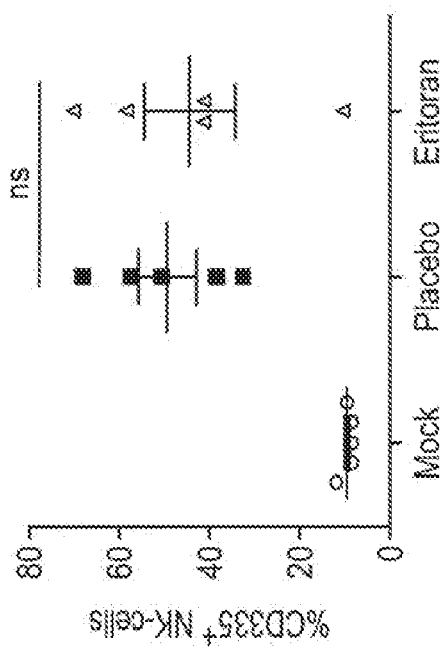

FIG. 5. Eritoran treatment reduces granulocyte and T-lymphocyte levels. FSC versus SSC plots from individual mice demonstrate an increase in the granularity of granulocytes (neutrophils) and absolute counts in EBOV-infected mice, which is indicative of neutrophil activation.

FIG. 6. Cytokine and chemokine levels were quantified in EBOV-infected and placebo groups. Eritoran treatment was associated with a reduction in Th1-associated TNFα and Th2-associated cytokines (e.g., IL-6, IL-7, IL-9, IL-10, and IL-13). Eritoran treatment was also associated with a reduction in the production of certain chemokines (e.g., IP-10 (CXCL10), MIG (CXCL9), MIP-1α (CCL3), MIP-10 (CCL4), MIP-2 (CXCL2), RANTES (CCL5), and LIF).

FIG. 7. Eritoran treatment activates neutrophils in peripheral blood. Comparisons of neutrophil populations in mock, placebo, and eritoran-treated mice. (A) Percentages of $CD11b^+$ cells positive for CD64: primary data (left) and quantitative data (right). (B) Percentages of $CD11b^+Ly6G/Ly6C^+$ positive for CD69: primary data (left) and quantitative data (right). (C) Ratios of neutrophils to total lymphocytes determined by dividing the percentages of $CD11+Ly6G/Ly6C^+$ by total lymphocytes (based on FSC versus SSC). (D) Ratios of neutrophils to $CD3^+$ T-lymphocytes determined by dividing the percentages of $CD1 1+Ly6G/Ly6C^+$ by $CD3^+$ T-lymphocytes. (E) Percentages of $CD11b^+$ cells positive for $Ly6G/Ly6C^+$. Mean values±SE based on 5 mice per group.

FIG. 8. Eritoran treatment reduces T-lymphocytes and the percentages of cells staining positive for Th1 and Th17 associated cytokines. (A)-(C) Percentages of the indicated T-cell populations positive for the indicated markers of activation in mock, placebo and eritoran-treated groups: representative primary data (left) and quantitative data (right). (A) $CD3+CD8^+$ T-cells positive for IFNγ. (B) $CD3+CD4^+$ T-cells positive for IFNγ. (C) $CD3+CD4^+$ T-cells positive for IL-17. (D) $CD3+CD4^+$ T-cells positive for IL-4. (E) $CD4+CD3^+$ T-cells positive for CD69. Mean values±SE based on 5 mice per group on day 6 post-infection. (F) Absolute counts of $CD3^+$ T-cell subsets in white blood cells.

FIG. 9. Percentages of PBMC subsets and activation of $CD8^+$ T-cells. Percentages of peripheral blood (A) $CD19^+$ B-cells, (B) $CD335^+$ NK cells, and (C) $CD14^+$ monocytes determined by flow cytometry on day 6 post ebola virus infection following red blood cell lysis. (D) Percentages of $CD69^+$ (activated) $CD8^+$ T-cells determined by flow cytometry 6 days following ebola virus challenge. Mean values±SE based on 5 mice per group.

FIG. 10. Eritoran protects mice from lethal MARV challenge. C57BL/6J mice were challenged via i.p. route with 1,000 PFU of mouse adapted MARV. Mice received 10 daily injections of eritoran or placebo (vehicle) via i.p. route. (A) Survival curves generated from MARV-infected mice treated with placebo or eritoran. (B) Assigned clinical scores. (C) Weight change following MARV challenge. Panels (A)-(C), mean values of two independent experiments of 5 mice per group with ±SE.

DETAILED DESCRIPTION OF THE INVENTION

The innate immune system is the first line of defense against invading microorganisms. Immune competent cells, such as macrophages, dendritic cells, neutrophils, and endothelial cells recognize pathogen-associated molecular patterns (PAMPS) on the surface of pathogens, as diverse as Gram-positive and Gram-negative bacteria, viruses, fungi, and *Mycoplasma*. The toll-like receptors (TLRs) are a family of closely related receptors that trigger cellular innate immune signaling pathways in response to discreet stimuli defined by conserved PAMPS. To date, ten different human TLRs have been identified. TLR4 is typically associated with activating innate immune signaling in response to lipopolysaccharide (LPS) produced during infection by Gram-negative bacteria. It was previously shown, however, that TLR4-deficient mice were strongly resistant to infection by a mouse-adapted strain of influenza, A/PR/8/34. Nhu et al., *Mucosal Immunology* 3(1):29-39, (2010). TLR4 mutant mice have also been shown to display natural resistance to acid-induced acute lung injury. Imai et al., *Cell* 133:235-249 (2008). However, there are no studies indicating whether inhibition of TLR4 in infected subjects may provide potential therapeutic effects following EBOV infection. Indeed, the only studies that report an interaction between EBOV and TLR4 include experiments in cell lines. For example, it was previously reported that EBOV glycoprotein (GP) induced the expression of IL-6, TNF-α, and IFN-β RNA to levels similar to those induced by LPS in HEK293-TLR4/MD2 cells. Okumura et al., *J. Virol.* 84(1):27-33 (2010). Additionally, Okumura reported that EBOV GP co-precipitated with TLR4 from co-transfected 293T cells, confirming that EBOV GP physically interacts with TLR4. Escudero-Perez further characterized the EBOV GP/TLR4 relationship by investigating GP shed from infected cells. Escudero-Perez et al., *PLoS* 10(11):e1004509 (2014). Noting the high amounts of shed GP detected in the blood of patients infected with EBOV, Escudero-Perez pre-treated dendritic and macrophage cells with mouse anti-TRL4 antibody (HTA125) and then incubated those same cells with shed GP. Binding of shed GP to both dendritic and macrophage cells was reduced upon treatment of the cells with anti-TLR4 antibody, suggesting that shed GP binding to dendritic cells and macrophages likely involves interaction with TLR4. Pre-treatment of cells with an anti-TLR4 antibody also considerably reduced the release of TNF-α, IL-6, IL-10, IL-8, IL-1f, and IL-1RA.

Eritoran (also known as E5564, compound 1287, SGEA or (α-D-Glucopyranose, 3-O-decyl-2-deoxy-6-O-[2-deoxy-3-O-[(3R)-3-methoxydecyl]-6-O-methyl-2-[[(-11Z)-1-oxo-11-octadecenyl)amino]-4-O-phosphono-3-D-glucopyranosyl]-2-[(1,3-dioxotetradecyl)amino]-1-(dihydrogen phosphate)) has previously been shown to be an effective antagonist of TLR4. This drug is described as compound 1 in U.S. Pat. No. 5,681,824, which is incorporated herein by reference for its description of compound 1 and methods of making same. Eritoran, has the structure of formula (I):

and may be provided as one of a number of pharmaceutically acceptable salts. The compound of formula (I) may be prepared in the form of a micelle, as described in U.S. Pat. No. 6,906,042, which is incorporated herein by reference in its entirety for the description of such micelles and methods for preparing same. In a preferred embodiment, eritoran is provided as a tetrasodium salt.

The present invention is directed to a method for treating a patient infected with EBOV comprising: administering to the infected patient in need of said treatment a therapeutically effective amount of eritoran or a pharmaceutically acceptable salt thereof. In another embodiment, the invention provides a method of treating EBOV infection in an animal by administering to the animal an inhibitor of TLR4. One embodiment of the present invention pertains to a method for treating a patient infected with a filovirus comprising: administering to the infected patient in need of said treatment a composition comprising an active ingredient and a pharmaceutically acceptable carrier wherein the active ingredient comprises eritoran or a pharmaceutically acceptable salt thereof.

A generalized reduction in the global release of inflammatory mediators in response to filovirus-infection following eritoran treatment may alleviate pathogenic features of disease associated with an over-active immune response. In this regard, a recent study indicated that a moderate decrease of inflammatory mediators correlated with survival in bacterial sepsis. Surbatovic et. al. *Sci Rep* 5:11355 (2015). Fatalities in EBOV infection have been associated with high levels of the pro-inflammatory cytokine IL-6, chemokines and the anti-inflammatory cytokine IL-10 in Falasca et al., *Cell Death and Diff* 22:1250-1259 (2015) and Baize et al. *Clin Exp Immunol* 128:163-8 (2002). Eritoran reduced both IL-6 and IL-10 in these studies, in addition to inhibiting chemokine production (FIGS. 12C & 12D).

Compounds suitable for use with the methods of the present invention include inhibitors of TLR4. In a preferred embodiment of the present invention, methods of the present invention are practiced using eritoran or a pharmaceutically acceptable salt thereof to inhibit TLR4 signaling. Eritoran is a synthetic lipid A analog that interferes with LPS signaling through TLR4. Eritoran and pharmaceutically acceptable salts thereof competitively inhibit LPS to bind the hydrophobic pocket of MD-2. When bound, eritoran or a pharmaceutically acceptable salt thereof prevents TLR4 dimerization and intracellular signaling.

In one embodiment of the present invention, treatment with eritoran or a pharmaceutically acceptable salt thereof decreases ebola induced pathology. Symptoms associated with EBOV infection include among others fever, headache, sore throat, diarrhea, vomiting, muscle pains, joint pains, skin rash, internal or external bleeding or combinations thereof. In addition, treatment with eritoran or a pharmaceutically acceptable salt thereof in the days following infection according to the invention disclosed herein may also lead to reduced systemic effects of EBOV infection. In one embodiment of the invention, EBOV-induced increases in liver enzyme levels are reduced by treatment with eritoran or a pharmaceutically acceptable salt thereof.

EBOV infection results in the expression of a multitude of cytokines. Excessive inflammation triggered by the virus infection can result in significant pathology. In another embodiment of the present invention, TLR4 is antagonized to decrease expression of EBOV-induced cytokine RNA expression in EBOV-infected subjects. In one embodiment of the present invention, the TLR4 antagonist, eritoran or a pharmaceutically acceptable salt thereof may result in a decrease in the production of EBOV-induced cytokine RNA expression in infected subjects. Without wishing to be bound to any particular theory, it is believed that EBOV infects cells and activates cellular signaling pathways that drive the production of inflammatory cytokines.

According to the present invention, the TLR4 pathway may be targeted by eritoran to reduce production of inflammatory cytokines in subjects infected with EBOV. In one embodiment of the invention, eritoran or a pharmaceutically acceptable salt thereof is used to reduce EBOV-induced expression of TNF-α, IL-6, IL-7, IL-9, IL-10, IL-13 or combinations thereof. Methods of the present invention may also be used for decreasing TLR4-mediated expression of IP-10, MIG, MIP-1α, MIP-1β, MIP-2, RANTES, LIF or combinations thereof. Further, methods of the present invention may be used to cause an increase in G-CSF, KC or combinations thereof. Methods of the present invention may also be used for decreasing granulocyte and T-lymphocyte cells in the EBOV-infected patient by administering eritoran or a pharmaceutically acceptable salt thereof. In yet a further embodiment, methods may cause a decrease in CD3+ T-lymphocyte cells in the EBOV-infected patient.

In yet another embodiment of the present invention, the effects of eritoran or a pharmaceutically acceptable salt thereof result in decreased EBOV replication in infected subjects compared to untreated subjects. While not wishing to be bound to any particular theory, it is believed that eritoran or a pharmaceutically acceptable salt thereof s inhibitory effects on TLR4 signaling produces a cellular environment that is less suitable to virus growth. Accordingly, one embodiment of the invention is directed to methods of administering eritoran or pharmaceutically acceptable salts thereof to cause a decrease in viral titers in the EBOV-infected patient.

Methods of the present invention may be used to treat any strain of EBOV infection. According to one embodiment of the present invention, the methods pertain to treatment for *Bundibugyo ebolavirus* strains. According to one embodiment of the present invention, the methods pertain to treatment for *Reston ebolavirus* strains. According to one embodiment of the present invention, the methods pertain to treatment for *Sudan ebolavirus* strains.

According to one embodiment of the present invention, the methods pertain to treatment for Taï Forest ebolavirus strains. According to one embodiment of the present invention, the methods pertain to treatment for *Zaire ebolavirus* strains. In addition, methods of the present invention may also be used to treat other filoviruses or other filovirus family members, including cuevavirus and Marburg virus.

According to one embodiment of the invention, the method of the present invention includes detecting the presence of EBOV infection in the specimens of a subject. A number of different laboratory diagnostic tests can be used for detecting the presence of EBOV in specimens, including direct antigen detection tests, virus isolation in cell culture, detection of EBOV-specific RNA (e.g., Nucleoprotein (NP) RNA) by real-time reverse transcriptase-polymerase chain reaction (rRT-PCR) or others.

According to the methods of the present invention, treatment may begin within up to about 2 days, about 3 days, about 4 days, about 5 days, about 6 days, about 7 days, about 1.5 weeks, about 2 weeks, about 2.5 weeks, or about 3 weeks following infection with EBOV or at the onset of clinical symptoms. According to a more preferred embodiment of the present invention, treatment may begin within up to about 2 days following infection with EBOV. The present invention relates to methods of treating subjects suffering from a virus infection, or more specifically subjects suffering from EBOV infection.

Administration of eritoran or a pharmaceutically acceptable salt thereof according to the present invention is typically carried out over the course of several days. The efficacy of the methods of the present invention have been shown to increase in a dose dependent manner, with higher dosages providing more effective treatment for infection. A single dose may be administered from between 1 µg to approximately 240 mg. In one embodiment, a single dose may be administered from between 1 µg to approximately 50 mg. In another embodiment a single dose may be administered from between 1 µg to approximately 70 mg.

In yet another embodiment, a single dose may be administered from between 1 µg to approximately 90 mg. In yet another embodiment, a single dose may be administered from between 1 µg to approximately 125 mg. In yet another embodiment, a single dose may be administered from between 1 µg to approximately 150 mg. In yet another embodiment, a single dose may be administered from between 1 µg to approximately 200 mg. The appropriate amounts of which can be determined by one of skill in the art according to the characteristics of the infected subject and the preferred route of administration.

In the methods of the invention, eritoran or a pharmaceutically acceptable salt thereof may also be administered to patients by intravenous infusion over a period of 12-100 hours, e.g., 60-80 or 72 hours. The infusion dosage rate may vary, for example, 0.001-0.5 mg/kg body weight/hour, e.g., 0.01-0.2 mg/kg/hour or 0.03-0.1 mg/kg/hour. The infusion of eritoran or a pharmaceutically acceptable salt thereof can, if desired, be preceded by a bolus injection of eritoran or a pharmaceutically acceptable salt thereof, which can be given at a dosage of 0.001-0.5 mg/kg body weight. The total amount of eritoran or a pharmaceutically acceptable salt thereof administered to a patient can be, for example, 50-600 mg of drug, e.g., 150-500 mg, by infusion over a period of 60-80 hours.

In another embodiment, eritoran or a pharmaceutically acceptable salt thereof may be administered to patients by intravenous infusion over a period of 1-10 hours for a total daily dose of between 1-20 mg. For example, the total amount of eritoran or pharmaceutically acceptable salt thereof administered to a patient may be between about 1 and about 10 mg in a daily dose, administered by intravenous infusion over a period of up to 5 hours. In one embodiment, the total amount of eritoran or a pharmaceutically acceptable salt thereof administered to a patient is 5 mg in a daily dose, administered by intravenous infusion over a period of about 1 hour. In one embodiment, the total amount of eritoran or a pharmaceutically acceptable salt thereof administered to a patient is 5 mg in a daily dose, administered by intravenous infusion over a period of about 4 hours.

The quantity and method of administration may vary during the course of treatment. For example, a patient may first receive eritoran or a pharmaceutically acceptable salt thereof by intravenous injection during the initial stage of infection to be followed by inhalation methods of administration for a series of days, including up to about 14 days post-infection.

Appropriate frequency of administration may also be determined by one of skill in the art. For example, the drug may be administered 1-4 times per day, preferably 2-4 times per day. Administration may be continuous over a selected period of time or may be in a series of spaced doses. Administration of the drug may continue until symptoms of the infection have disappeared. In some cases, it may be preferable to continue administration for several days. In one embodiment, administration may continue for several days after clinical symptoms of infection have disappeared. It will be understood that specific dosage ranges and pharmaceutical formulations may vary according to the method of administration and the specific physical characteristics of the subject being treated.

In order to more clearly and concisely describe the subject matter of the claims, the following definitions are intended to provide guidance as to the meaning of terms used herein.

As used herein, the articles "a" and "an" mean "one or more" or "at least one," unless otherwise indicated. That is, reference to any element of the present invention by the indefinite article "a" or "an" does not exclude the possibility that more than one of the element is present.

Values and ranges are recited in collection with various embodiments of the present invention, e.g., amount of a compound of formula (I) present in a composition. It is to be understood that all values and ranges which fall between the values and ranges listed are intended to be encompassed by the present invention unless explicitly stated otherwise.

The term "effective amount" of a compound refers to a sufficient amount of the compound that provides a desired effect but with no- or acceptable-toxicity. This amount may vary from subject to subject, depending on the species, age, and physical condition of the subject, the severity of the disease that is being treated, the particular compound used, its mode of administration, and the like. A suitable effective amount may be determined by one of ordinary skill in the art.

"Treatment", "treat", or "treating" as used herein, are defined as the application or administration of a therapeutic agent to a subject, or to an isolated tissue or cell line from a subject. The subject generally has a disease or disorder, a symptom of disease or disorder or a predisposition toward a disease or disorder (e.g., EBOV). Specifically as used herein, treatment is directed at subjects already infected with a virus, such as EBOV, as opposed to subjects that have not yet been infected. The purpose of treatment is generally to cure, heal, alleviate, relieve, remedy, ameliorate, or improve such disease, disorder, or symptoms. "Treated", as used herein, refers to the disease or disorder being cured, healed, alleviated, relieved, remedied, ameliorated, or improved.

Compounds suitable for use with the methods of the present invention are administered in therapeutically effective dosages. The term "therapeutically effective amount" is used to indicate an amount of an active compound, or pharmaceutical agent, that elicits the biological or medicinal response indicated. This response may occur in a tissue, system (animal including human) that is being sought by a researcher, veterinarian, medical doctor or other clinician.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al., describe pharmaceutically acceptable salts in detail in *J. Pharmaceutical Sciences,* 66: 1-19 (1977).

The salts can be prepared in situ during the final isolation and purification of the compounds taught herein, or separately by reacting a free base or free acid function with a suitable reagent, as described generally below. For example, a free base function can be reacted with a suitable acid. Furthermore, where the compounds taught herein carry an acidic moiety, suitable pharmaceutically acceptable salts thereof may, include metal salts such as alkali metal salts, e.g., sodium or potassium salts; and alkaline earth metal salts, e.g., calcium or magnesium salts. Sodium salts of compounds within the scope of formula I are described, for example, in U.S. patent application Ser. No. 12/516,082 and U.S. Patent Application Publication No. 2008/0227991. Examples of pharmaceutically acceptable, nontoxic acid addition salts are salts formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. In some embodiments, the compound of formula (I) is a sodium salt, e.g., a tetrasodium salt.

The term "subject" refers to an animal, preferably a mammal, and most preferably a human, who is the object of treatment, observation or experiment. The mammal may be selected from the group consisting of mice, rats, hamsters, gerbils, rabbits, guinea pigs, dogs, cats, sheep, goats, cows, horses, giraffes, platypuses, primates, such as monkeys, chimpanzees, and apes. In some embodiments, the subject is a human.

As used herein, the terms "antagonist" and "inhibitor" refer to molecules or compounds that inhibit the action of a "native" or "natural" molecules or compounds.

In some embodiments, the compounds described herein are administered systemically. As used herein, "systemic administration" refers to any means by which the compounds described herein can be made systemically available. In some embodiments, systemic administration encompasses intravenous administration, intraperitoneal administration, intramuscular administration, intracoronary administration, intraarterial administration (e.g., into a carotid artery), intradermal administration, subcutaneous administration, transdermal delivery, intratracheal administration, subcutaneous administration, intraarticular administration, intraventricular administration, inhalation (e.g., aerosol), intracerebral, nasal, naval, oral, intraocular, pulmonary administration, impregnation of a catheter, by suppository and direct injection into a tissue, or systemically absorbed topical or mucosal administration. Mucosal administration includes administration to the respiratory tissue, e.g., by inhalation, nasal drops, ocular drop, etc.; anal or vaginal routes of administration, e.g., by suppositories; and the like. In some embodiments, the compounds described herein are administered intravenously. In other embodiments, the compounds described herein are administered orally. In some embodiments, the compounds described herein may be administered intravenously one to five times a week. In some other embodiments, the compounds described herein may be administered orally one or more times a day (e.g., once a day, twice a day or three times a day). In yet other embodiments, the compounds described herein may be administered intraperitoneally one or more times a day.

In further embodiments, the treatment regime may last from about 1, about 2, about 3, about 4, about 5, about 6, about 7, about 8, about 9, or about 10 days.

Pharmaceutical formulations suitable for use with the present invention may also include excipients, preservatives, pharmaceutically acceptable carriers and combinations thereof. the term "pharmaceutically acceptable carrier or excipient" means a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols. The compositions can additionally include lubricating agents such as talc, magnesium stearate, and mineral oil; wetting agents; emulsifying agents; suspending agents; preserving agents such as methyl-, ethyl-, and propyl-hydroxy-benzoates; pH adjusting agents such as inorganic and organic acids and bases; sweetening agents; and flavoring agents.

Methods of the present invention may also be used in combination with other treatment regimes. For example, one embodiment of the present invention pertains to combination therapy in which eritoran or a pharmaceutically acceptable salt thereof is used in combination with supportive care, such as rehydration. Additionally, one embodiment of the present invention pertains to combination therapy in which eritoran or a pharmaceutically acceptable salt thereof is used in combination with a therapeutically effective amount of an antiviral compound.

EXAMPLES

Example 1

Animal Challenge and Treatment

All work with EBOV was performed in BSL-4 facilities of the Galveston National Laboratory. Flow cytometry was performed following inactivation with 4% paraformaldehyde in PBS for 48 hours according to the University of Texas Medical Branch standard operating procedure and removed from BSL-4 for analysis with LSRII Fortessa flow cytometer (BD Biosciences) available at the University of Texas Medical Branch Flow Cytometry Core Facility. To remove serum samples from EBOV-infected mice, samples were gamma-irradiated with the 5 Mrad dose according the University of Texas Medical Branch standard operating procedure protocol. The staff had the U.S. government permissions and appropriate training for work with EBOV.

EBOV infection of mice was performed in the ABSL-4-containment facilities at the Galveston National Laboratories in accordance with the University of Texas Medical Branch Institutional Animal Care and Use Committee. Wild-type C57BL/6J mice, TLR4$^{-/-}$ and TNFR1/2$^{-/-}$ mice were purchased from Jackson Laboratories. Mice (8-10 weeks) were infected with 1000 pfu mouse-adapted EBOV strain or mouse adapted Marbug strain Mayinga Ci67 (PMID21289122) by intraperitoneal injection. All virus stocks were back-titrated at time of challenge to verify viral titers. Eritoran was prepared as described by the manufacturer and diluted to a final concentration of 2.33 mg/mL (Eisai). Mice received daily administration consisting of 100 µL of placebo (vehicle) or eritoran at an effective dose of 233 µg/day. Mice were monitored twice daily from day 0 to day 14 post challenge, followed by once daily monitoring from day 15 to the end of the study at day 28. The disease was scored using the following parameters: dyspnea (possible scores 0-5), recumbency (0-9), unresponsiveness (0-5), and bleeding/hemorrhage (0-5). All mice were euthanized at day 28 post EBOV-challenge.

Analysis of Viremia

Total RNA was isolated from serum samples taken at Day 6 post-EBOV-challenge using QIAamp Viral RNA mini kit as per manufacturer's protocol (Qiagen). Absolute quantification of the Nucleoprotein (NP) gene was performed using One-step RT-ddPCR Advanced kit for probes (Bio-Rad), with probes specific for the NP gene fragment corresponding to nucleotides 2,095-2,153 of EBOV genomic RNA, GenBank Accession No. AF086833 using forward primer GCCACTCACGGACAATGACA, reverse primer GCATGCGAGGGCTGGTT, and probe FAM-AGAAAT-GAACCCTCCGGCT-MBG. Briefly, 50 µg of RNA was added to 5 µl of supermix, 2 µl of Reverse transcriptase enzyme, 1 µl of 300 mM DTT, and 1 µl of 20×NP custom Taqman assay (Life Technologies) for each sample. ddPCR reaction mixtures were loaded onto cartridges to create droplets on a QX200 Droplet Generator (BioRad). The droplets were transferred onto 96-well PCR Plates (Eppendorf, Hauppauge, N.Y.) and amplified on a C1000 Thermal Cycler with 96-Deep Well Reaction Module (BioRad). The cycle conditions were 42° C. for 60 min, 95° C. for 10 min, followed by 39 cycles of 95° C. 15 sec and 60° C. for 1 min, and a final enzyme deactivation step of 98° C. for 10 min. Finally, the PCR plates were loaded onto a Droplet Reader, which quantified the number of positive and negative droplets in each sample. Analysis was performed using QuantaSoft software to get the final concentrations in each sample.

Analysis of Neutrophils and T Cells in the Peripheral Blood by Flow Cytometry

Erythroyctes were lysed using lytic lysis buffer as recommended by the manufacturer (Sigma Aldrich). Cells were pelleted at 400×g, washed in phosphate buffered saline containing 2% fetal bovine serum, and stained with the following antibodies: panel 1, CD3-BUV.395 (145-2C11, BD Biosciences), CD4-PerCP.Cy5.5 (RM4-5, BD Biosciences), CD8-BVLT.421 (53-6.7, BD Biosciences), IFNγ-Alexa.488 (XMG1.2, BD Biosciences), IL17A-PE (TC11-18H10.1, BD Biosciences), IL4-APC (11B11, BD Biosciences), panel 2, CD11b-Alexa.488 (M1/70, BioLegend), Ly6G/Ly6C.Alexa.647 (RB6-8C5, BioLegend), CD64.BVLT.421 (X54-5/7.1, BioLegend), CD69-PE (H1.2F3, BioLegend), CD3-BUV.395, CD4-PerCP.Cy5.5, panel 3, CD19-APC (1D3, BD Biosciences), CD14-BUV.737 (rmC5-3, BD Biosciences) and CD335-FITC (29A1.4, BD Biosciences). For determination of absolute counts, CountBright Absolute Counting Beads (ThermoFisher Scientific) were used as per manufacturer's instructions. Data was collected using LSRII Fortessa flow cytometer (BD Biosciences) and analyzed with FlowJo.

Analysis of Cytokines, Chemokines, and Free Radicals in the Peripheral Blood

Serum samples collected on Day 6 post-infection were irradiated, taken out of BSL-4, and analyzed using the Multiplex-32 magnetic bead-based assay (Millipore) by Eve Technologies. Total free radicals were measured using the OxiSelect In Vitro ROS/RNS Assay Kit (Cell BioLabs) using the protocol provided by the manufacturer.

Statistical Analysis

Analysis was performed using Graphpad Prism software (version 6.04). Comparison of survival curves was conducted using Long-rank (Mantel-Cox) test. A paired t-test (one sided) was used to compare the levels of viremia, cytokines, chemokines, and free radicals in plasma and differences in the percentages of immune cells between groups.

Example 2

C57BL/6J mice between the ages of 7-8 weeks were infected with 1000 pfu mouse adapted EBOV via intraperitoneal injection at Day 0, which routinely results in 100% rates of death within 7 days of challenge. Mice then received ten consecutive daily doses consisting of intraperitoneal injections administering 233 µg eritoran (E5564) or vehicle starting at Day 0. Each mouse was weighed and clinically scored daily for symptoms associated with disease progression. Once signs of disease progression were observed, mice were monitored twice daily. Mice receiving a score a total score of 8, or 3 in any individual category, were promptly euthanized per institutional protocol. 100% of mice receiving the placebo died or met criteria for euthanization by day 7 following challenge (FIG. 1B). Of the mice receiving daily eritoran treatment, 70% survived until the end of the study, 28 days post-challenge (p<0.0001). Based on these results, it was concluded that TLR4$^{-/-}$ mice would survive lethal EBOV-challenge. However, TLR4$^{-/-}$ mice remained as susceptible to EBOV as wildtype mice. As indicated in FIG. 1C, clinical scores parallel the survival curves with mice receiving placebo exhibiting increased scores in comparison to eritoran-treated mice beginning from the symptomatic stage of disease (Day 6). Weight loss was observed in both placebo and eritoran-treated mice. However, eritoran-treated mice returned to normal weight following a period of recovery with an overall improvement in clinical score being observed following Day 8 (FIG. 1D). Quantitative RT-PCR-based analysis of viremia demonstrated that eritoran treatment reduced it by two-logs (from $10^7$ to $10^5$ genome equivalents per mL) (FIG. 1E).

Flow cytometry-based analysis of PBMCs revealed a striking difference between both groups of EBOV-infected mice and PBMCs from uninfected mice (FIG. 2A). A clear increase in the granularity associated with granulocytes was evidence following FSC×SSC analysis (indicated as Neutrophils on plots following subsequent confirmation staining). It was determined that these findings were associated with the activation of neutrophils. Eritoran treatment blocked expansion of the neutrophil population, with regards to absolute counts, despite a similar increase in granularity and activation being observed (FIG. 2B). Granulocytes increased from 2,070 cells/μl in mock samples to 9,485 cells/μl in the placebo group ($p<0.013$) whereas a limited increase to 2,786 cells/μl was observed in eritoran-treated mice (n.s.). Further analysis of the gated granulocyte subset revealed that the majority of this population was double $CD11b^+Ly6G/Lyc6C^+$ neutrophils with no difference in the percentages of neutrophils being detected in the placebo and eritoran groups (FIG. 7E).

Treatment with eritoran significantly increased the percentages of neutrophils expressing the activation markers CD64 (FIG. 7A) and CD69 (FIG. 7B), despite the reduction in the number of granulocytes. The ratio of $CD11b^+Ly6G/Ly6C^+$ neutrophils to total lymphocytes increased from 0.19 in mock-infected mice to 1.39 in the placebo group and 2.15 in eritoran-treated mice (FIG. 7C). Similarly, the ratio of $CD11b^+Ly6G/Ly6C^+$ neutrophils to $CD3^+$ T-lymphocytes increased from 1.41 in mock-infected mice to 5.26 in the placebo group and 11.05 in eritoran-treated mice (FIG. 7D). Taken together, these findings indicate that treatment with eritoran reduces granulocytosis and results in a higher percentage of activated $CD11b^+Ly6G/Ly6C^+$ neutrophils.

Based on the decreased ratio of $CD3^+$ T-cells to neutrophils in eritoran-treated mice, T-lymphocyte subsets $CD3^+$, CD3+CD4+, and $CD3+CD8^+$ T cells were examined. Infection with EBOV resulted in the reduction of all these populations, that is consistent with lymphopenia, a hallmark of EBOV-infections in both humans and animal models of EVD (FIG. 2C). Unexpectedly, treatment with eritoran further reduced the absolute count of all the three lymphocyte populations, as analyzed on Day 6. The relative activation status of gated $CD8^+$ and $CD4^+$ T-cells were studied by analyzing subsets secreting Th-associated cytokines and subsets expressing markers of activation. EBOV infection increased the percentages of $CD8^+$ and $CD4^+$ T cells positive for IFNγ by 4.1-fold (FIG. 8A) and 3.7-fold (FIG. 8B), respectively. The infection similarly increased the percentages of $CD4^+$ T cells positive for IL-17A by 3.0-fold (FIG. 8C), but did not change the percentages of $CD4^+$ T cells positive for IL-4 (FIG. 8D) or the activation marker CD69 (FIG. 8E). These data demonstrate the induction of Th1/Th17 type response following infection of mice with EBOV. Treatment with eritoran dramatically reduced the levels of IFNγ-secreting CD8+(FIG. 8A) and $CD4^+$ T cells (FIG. 8B) and IL-17A-secreting $CD4^+$ T cells, which almost reached the levels in mock-infected mice (FIG. 8C). On the other hand, eritoran treatment increased the percentages of $CD4^+$ T cells positive for IL-4 by 3.8-fold (FIG. 8D), and increased the percentages of CD4 T cells (but not $CD8^+$ T cells; FIG. 9D) positive for CD69 by 2.8-fold (FIG. 8E). Analysis of B-cells, NK-cells and monocytes demonstrated no effect of eritoran on these populations (FIGS. 9A-C). These data suggest that treatment with eritoran strongly blunts Th1 and Th17 responses and shifts the response toward Th2.

To further assess the effects of eritoran on Th-associated and global immunological responses, serum samples taken on Day 6 post-infection were assayed for cytokine/chemokine levels using a multiplex bead-based assay. As indicated in FIG. 3A and FIG. 6, distinctive patterns were observed between placebo and eritoran-treated mice. Specifically, EBOV infection resulted in an increase of most inflammatory markers assayed in both the placebo and eritoran treated groups in comparison to mock-infected mice. However, treatment with eritoran reduced the levels of several cytokines; whereas TNFα was the only Th1-associated cytokine reduced, multiple Th2-associated cytokines including IL-6, IL-9, and IL-10 and IL-13 were reduced in eritoran treated mice compared to mice receiving the placebo. The reduction in TNFα may be due in part to the direct inhibitory effects of eritoran as TNFα is a central effector molecule associated with the activation of the TLR4 signaling pathway. The only notable cytokines that were increased in eritoran treated mice were G-CSF and M-CSF. Due to the pleiotropic role of TNFα in the inflammatory response, the susceptibility of $TNFR1R2^{-/-}$ mice to EBOV-infection was assessed. No differences in disease and survival were observed between wild-type and $TNFR1R2^{-/-}$ mice. Although excess amounts or prolonged expression of TNFα may contribute to pathogenesis of disease, consistent with this result, TNFα also plays a central role in the regulation of immune response.

Consistent with the overall down-modulation of the inflammatory response observed in the previous analysis, a broad decrease in chemokine production was detected. MIP-1α, MIP-1β, RANTES, MIP-2, MIG, and IP-10 were all significantly decreased in eritoran-treated mice. Eritoran treatment, however, did result in a significant increase in the production of KC; a neutrophil chemoattractant secreted by macrophages, epithelial cells and activated neutrophils, which increased 10.0-fold.

Levels of cytokines associated with stem cell differentiation and progenitor development were either increased or reduced by eritoran treatment. Eritoran treatment increased the levels of G-CSF by 7.0-fold. G-CSF stimulates differentiation of progenitor stem cells towards granulocytes development. Similarly, though not statistically significant, eritoran treatment increased the levels of the macrophage differentiation factor, M-CSF, by 58%, although the increase was not statistically significant. Conversely, serum IL-7 levels was 41% reduced in eritoran-treated mice. IL-7 induces hematopoietic stem cell differentiation into lymphoid progenitor cells and promotes differentiation and survival of T-cells and NK cells. The reduction in IL-7 may contribute to the overall decrease in T-lymphocytes observed in eritoran-treated mice. Serum levels of leukemia inhibitory factor (LIF) decreased by 10.3-fold in eritoran-treated mice. This finding is particularly interesting as LIF expression levels inversely correlate with cellular differentiation; hence, a decrease in LIF levels in eritoran-treated mice is indicative of increased immune cell differentiation.

Figure 3A:
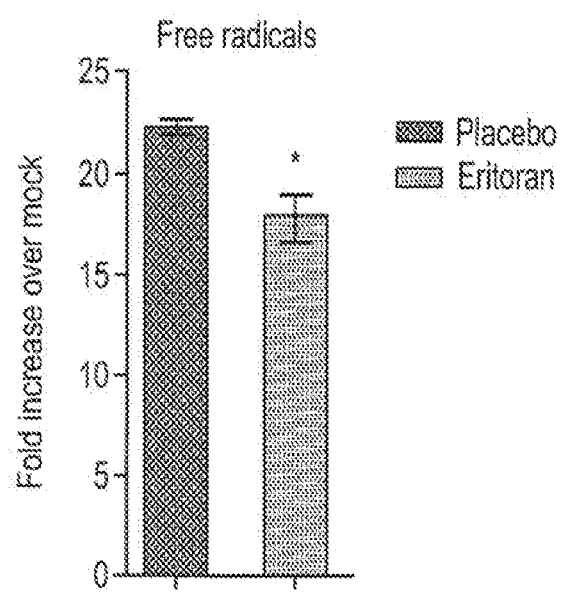

Lastly, serum samples for total levels of free radicals were analyzed using the OxiSelect In vitro reactive oxygen species/reactive nitrogen species (ROS/RNS) assay, which reacts with hydrogen peroxide ($H_2O_2$), peroxyl radical ($ROO^-$), nitric oxide (NO) and peroxynitrite ($ONOO^-$). Consistently with the previous observations, EBOV infection increased the levels of free radicals 22.3-fold (FIG. 3A). Interestingly, eritoran treatment partially reversed this, resulting in 23% reduction of free radicals. Overall, serum analysis revealed an altered extracellular milieu in eritoran-treated mice that is consistent with a broad down-regulation of mediators associated with the induction of a 'cytokine storm'.

Example 3

Figures 10A, 10B, 10C:
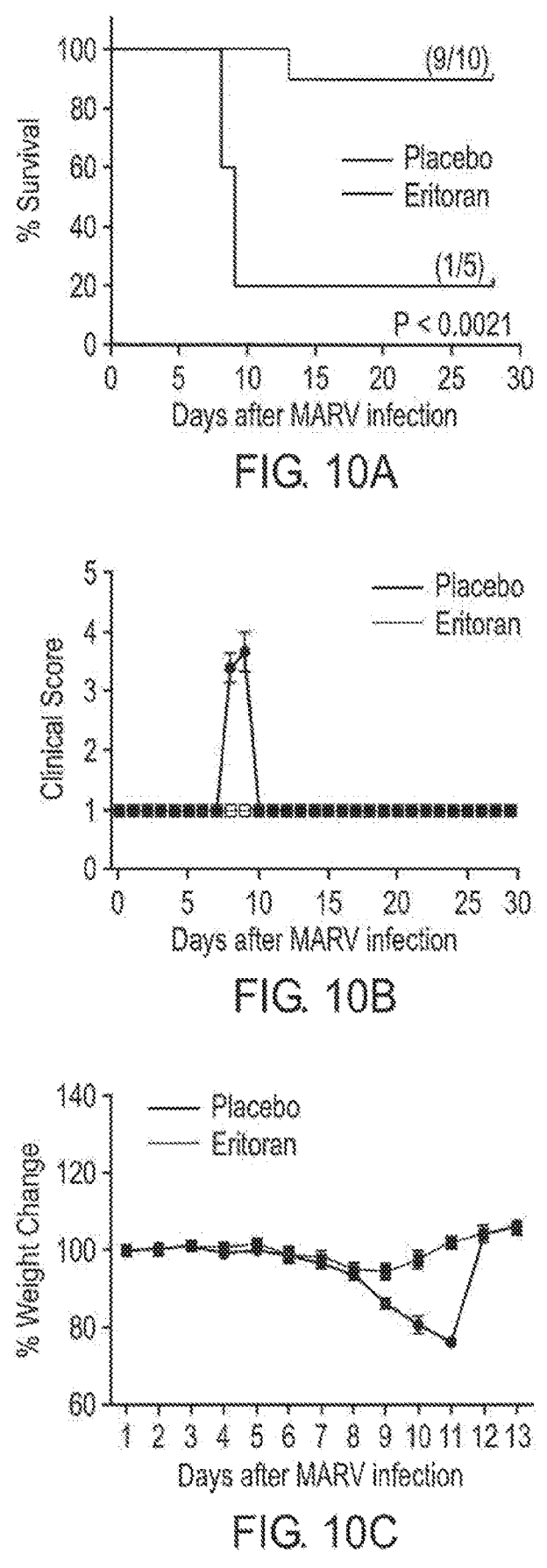

As filoviruses, a collective family of related viruses, share common features associated with bacterial sepsis, the ability of eritoran to protect mice from lethal MARV challenge was assessed. Mice were treated as indicated in the outline provided in FIG. 1A; however, mice were challenged with mouse adapted MARV at day 0. As indicated in FIG. 10A, 90% of infected mice survived lethal MARV challenge, whereas one mouse (20%) from the control group survived. The average clinical score for eritoran treated mice remained relatively unchanged as only the mouse that succumbed to infection received a score greater than 1 (FIG. 10B). Conversely, all mice in the control group received clinical scores of 3 or 4 at days 8 and 9 post-challenge. As observed in EBOV-infected mice, the average weight of control mice decreased considerably following MARV challenge (FIG. 10C); however, only a minimal reduction was observed in eritoran treated mice. Similar to the weight gains observed in EBOV-infected, eritoran treated mice, an increase in weight was observed in MARV-infected mice receiving eritoran treatment. Taken together, the data indicates that eritoran treatment is effective at promoting survival from lethal filovirus infections.

Illness caused by Marburg virus is associated with a series of symptoms. See the *Marburg haemorrhagic fever fact sheet published by the World Health Organization* at www.who.int/mediacentre/factsheets/fs_marburg/en/. Symptoms may being abruptly with high fever, severe headache and severe malaise. Patients commonly experience muscle aches and pains. On the third day, patients may exhibit severe watery diarrhea, abdominal pain and cramping, nausea and vomiting. The diarrhea may persist for a week, and patient may exhibit a "ghost-like" appearance of drawn features, deep-set eyes, expressionless faces, and extreme lethargy. Many patients develop severe haemorrhagic manifestations between five and 7 days after the onset of symptoms. Fresh blood may appear in vomit, feces, and draw from the nose, gums, and vagina. In a 1967 outbreak in Germany and Yugoslavia, patients exhibited a non-itchy rash between two and seven days after the onset of symptoms. In the late phase, about 15 days after the onset of symptoms, male patients may exhibit orchitis. Patients with an affected central nervous system may exhibit confusion, irritability, and aggression.

Fatal cases usually include bleeding, often from multiple areas. Death most often occurs between 8 and 9 days after the onset of symptoms and is usually preceded by severe blood loss and shock.

These findings indicate that TLR4 antagonism may provide an urgently needed therapeutic intervention strategy for the treatment of EBOV-infected patients. While a broad reduction in the overall inflammatory response was observed, the specific down-regulation of Th2 cytokines may represent a key mechanism of action associated with the increased survival of mice treated with eritoran. Furthermore, a generalized reduction in the overall response to EBOV infection may alleviate pathogenic features of disease associated with an over-active immune response. Fatalities in EBOV infection have been associated with high levels of the pro-inflammatory cytokine IL-6, chemokines and the anti-inflammatory cytokine, IL-10. Unexpectedly, Eritoran reduced both IL-6 and IL-10 in these studies, in addition to inhibiting chemokine production. Furthermore, disease progression in sepsis has been shown to be mediated by a shift from a pro-inflammatory Th1-response to anti-inflammatory, Th2-response. Hence, the pro-survival effects of eritoran observed in these studies may be associated with a sustained Th1 response as a result of the down-regulation of Th2-associated cytokines.

The reduction in the inflammatory response is likely directly associated with the inhibitory activity of eritoran, which is a TLR4-specific inhibitor. TLR4 is expressed in numerous cell types including both immune (e.g. both adaptive and innate immune cell subsets) and non-immune cells (e.g. intestinal epithelial cell lines). Hence, the broad reduction of inflammatory mediators may be due the global effects of eritoran. As demonstrated in bacterial sepsis, continued TLR4 stimulation results in an over-exacerbated immunological response, which ultimately elicits a more damaging than beneficial response.

However, as demonstrated in the present studies, the absence of TLR4 is equally detrimental following EBOV-challenge suggesting that the effects of eritoran may partially blunt the direct (GP) or indirect (OxPLs) association of EBOV with TLR4. Hence, a more limited induction of the TLR4 signaling pathway may result in beneficial immune responses.

Clear indications of neutrophil activation were detected in our analysis of PBMCs (FIG. 2A). Hence the lower number of neutrophils in peripheral blood of eritoran-treated mice may be due to increased tissue migration, increased turnover or reduced chemotactic signaling resulting in a decrease of neutrophil mobilization from the bone marrow. A decrease in inflammatory mediators known to induce neutrophil membrane rigidity (e.g. TNFα) may promote migration and reduce sequestration in vascular tissue as observed in animal models of bacterial sepsis. Similarly, lower levels of T-lymphocytes in peripheral blood may be the result of increased tissue migration due to the development of improved chemokine gradients. Furthermore, high levels of chemokines may confound proper tissue migration in the absence of eritoran treatment due to systemic release of these chemoattractants. A significant reduction in the majority of chemokines analyzed in these studies was observed. However, the particular effects of these reductions on neutrophil counts and/or migration remains to be determined.

Although these studies suggest a putative role of EBOV-mediated induction of TLR4 signaling, it is possible that eritoran protects EBOV-infected mice by reducing the inflammatory effects of oxidized phospholipids (Ox-PLs) rather than by blocking GP-mediated stimulation of TLR4.

Ox-PLs, which are generated following infections, apoptosis and tissue damage, have been shown to interfere with dendritic cell (DC) maturation resulting in limited lymphocyte activation. The resulting Ox-PLs exhibit profound modulatory effects on the inflammatory response triggering production of both pro- and anti-inflammatory mediators.

associated cytokines. Patients with severe bacterial sepsis have a low Th1:Th2 ratio whereas as the opposite is observed in nonseptic patients (Ferguson et al. *Intensive Care Med* 25:106-9 (1999)); hence, the reduced plasma viremia and improved survival with eritoran treatment may be due to a prolonged Th1-response.

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
gccactcacg gacaatgaca                                                    20

<210> SEQ ID NO 2
<211> LENGTH: 17
<212> TYPE: DNA
<213> ORGANISM: Artificial Sequence
<220> FEATURE:
<223> OTHER INFORMATION: primer

<400> SEQUENCE: 2
gcatgcgagg gctggtt                                                       17

<210> SEQ ID NO 3
<211> LENGTH: 19
<212> TYPE: DNA
<213> ORGANISM: Artificial Sequence
<220> FEATURE:
<223> OTHER INFORMATION: synthetic

<400> SEQUENCE: 3
agaaatgaac cctccggct                                                     19
```

The formation of Ox-PLs is consistent with the known activation of neutrophils and subsequent release of ROS following EBOV infection. It is feasible that Ox-PLs may further stimulate TLR4 signaling during the course of disease. This idea is supported by previous observations utilizing an influenza model of disease, which demonstrated eritoran antagonism of OxPLs was mediated by blocking interaction with TLR4. Shirey et al., *Nature* 497(7450):498-502 (2013).

The global reduction in inflammatory mediators indicates that eritoran blunts the development of a cytokine storm. Furthermore, bacterial infections causing sepsis are typically characterized by a shift from a Th1 response to a Th2-response as disease progresses (Aziz et al. *J Leukoc Biol* 93:329-42 (2013), which may also be the case for filovirus infection. The extracellular milieu in eritoran treated mice is suggestive of an extended Th1 response in comparison to serum cytokine analysis of the placebo group, which appear to have progressed to a Th2 response. Conversely, intracellular staining analysis indicates that a counter, Th2 response was being initiated at day 6 in eritoran treated mice as determined by an increase in IL-4-secreting CD4$^+$ T-cells in comparison to untreated, EBOV-infected mice. This can be explained by eritoran treatment delaying initiation of Th2 response, as noted by the significant decrease in Th2-

What is claimed is:

1. A method for reducing viremia in a patient infected with ebola virus comprising:
   administering to the infected patient in need of said treatment a therapeutically effective amount of eritoran or a pharmaceutically acceptable salt thereof.

2. The method of claim 1, wherein eritoran tetrasodium salt is administered.

3. The method of claim 1, further comprising administering to the infected patient a therapeutically effective amount of an antiviral compound.

4. The method of claim 1, wherein the infected patient is administered a therapeutically effective amount of eritoran or a pharmaceutically acceptable salt thereof following testing positive for the presence of ebola virus infection.

5. The method of claim 4, wherein the infected patient tested for the presence of ebola virus infection using PCR, rt-PCR direct antigen detection tests, virus isolation in cell culture, or combinations thereof.

6. The method of claim 1, further comprising causing a decrease in ebola-induced cytokine levels in the infected patient.

7. The method of claim 6, further comprising causing a decrease in ebola-induced cytokine levels in the infected patient wherein the cytokines comprise TNF-α, IL-6, IL-7, IL-9, IL-10, IL-13 or combinations thereof.

8. The method of claim 1, further comprising causing a decrease in ebola-induced chemokine levels in the infected patient wherein the chemokines comprise IP-10, MIG, MIG, MIP-1α, MIP-1β, MIP-2, RANTES, LIF or combinations thereof.

9. The method of claim 1, further comprising causing an increase in ebola-induced stimulating factor levels in the infected patient wherein the stimulating factor is G-CSF, KC or combinations thereof.

10. The method of claim 1, further comprising causing a decrease in granulocyte and T-lymphocyte cells in the infected patient.

11. The method of claim 10, further comprising causing a decrease in CD3' T-lymphocyte cells in the infected patient.

12. The method of claim 1, wherein the infected patient is administered a therapeutically effective amount of eritoran or a pharmaceutically acceptable salt thereof following the onset of clinical symptoms, wherein the clinical symptoms comprise fever, headache, sore throat, diarrhea, vomiting, muscle pains, joint pains, skin rash, internal or external bleeding or combinations thereof.

13. The method of claim 1, wherein eritoran or a pharmaceutically acceptable salt thereof is administered by one of the routes comprising intravenous administration, intraperitoneal administration, intramuscular administration, intracoronary administration, intraarterial administration, intradermal administration, transdermal delivery, intratracheal administration, subcutaneous administration, intraarticular administration, intraventricular administration, inhalation, intracerebral, nasal, naval, oral, intraocular, pulmonary administration, impregnation of a catheter, by suppository and direct injection into a tissue, or systemically absorbed topical or mucosal administration.

14. The method of claim 13, wherein eritoran or a pharmaceutically acceptable salt thereof is administered intravenously.

15. The method of claim 1, wherein the effects of administering eritoran or pharmaceutically acceptable salts thereof cause a decrease in viral titers in the infected patient.

16. The method of claim 1, wherein the infected patient is administered a therapeutically effective amount of eritoran or a pharmaceutically acceptable salt thereof in a range of from between about 1μg to about 240 mg, per dose.

* * * * *